(12) United States Patent
Muller

(10) Patent No.: US 7,678,131 B2
(45) Date of Patent: Mar. 16, 2010

(54) SINGLE-WIRE EXPANDABLE CAGES FOR EMBOLIC FILTERING DEVICES

(75) Inventor: Paul F. Muller, San Carlos, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 545 days.

(21) Appl. No.: 11/655,311

(22) Filed: Jan. 19, 2007

(65) Prior Publication Data

US 2007/0149997 A1  Jun. 28, 2007

Related U.S. Application Data

(63) Continuation of application No. 10/285,322, filed on Oct. 31, 2002, now abandoned.

(51) Int. Cl.
*A61M 29/00* (2006.01)

(52) U.S. Cl. .................. 606/200; 606/198; 606/108; 604/93.01

(58) Field of Classification Search .......... 606/200, 606/198, 108; 604/93.01
See application file for complete search history.

(56) References Cited

U.S. PATENT DOCUMENTS

| | | |
|---|---|---|
| 3,952,747 A | 4/1976 | Kimmell, Jr. |
| 4,425,908 A | 1/1984 | Simon |
| 4,494,531 A | 1/1985 | Gianturco |
| 4,612,931 A | 9/1986 | Dormia |
| 4,619,246 A | 10/1986 | Molgaard-Nielsen et al. |
| 4,643,184 A | 2/1987 | Mobin-Uddin |
| 4,650,466 A | 3/1987 | Luther |
| 4,662,885 A | 5/1987 | DiPisa, Jr. |

(Continued)

FOREIGN PATENT DOCUMENTS

EP 0427429 A3 9/1991

(Continued)

OTHER PUBLICATIONS

Dilitation of the Carotid Artery By A Temporary Carotid Filter By A. Beck, St. Milic, A.M. Spagnoli, Nov.-Dec. Issue of OPLITAI An International Journal on Military Medicine and Health Emergencies, pp. 67-74, 1989.

*Primary Examiner*—Tan-Uyen T. Ho
*Assistant Examiner*—Jing Ou
(74) *Attorney, Agent, or Firm*—Fulwider Patton LLP

(57) ABSTRACT

A single-wire expandable cage for an embolic filtering device includes a single cage wire coupled to an elongated member, such as a guide wire, and adapted to expand from an unexpanded position to an expanded position in a patient's body vessel. The wire includes a first end and a second end which are coupled to the guide wire. A filter element is attached to the single-wire cage. The single-wire cage may be rotatably mounted to the guide wire or may be slidably disposed on the guide wire to allow the composite cage and filter element to be slid over the guide wire in an over-the-wire fashion once the guide wire is delivered to the target location in the patient's vasculature. One embodiment of the single-wire cage utilizes an offset arrangement in which the guide wire remains extended along the wall of the body vessel once the single-wire cage is deployed. Another embodiment of the device centers the guide wire within the body vessel.

20 Claims, 4 Drawing Sheets

U.S. PATENT DOCUMENTS

| | | |
|---|---|---|
| 4,688,553 A | 8/1987 | Metals |
| 4,706,671 A | 11/1987 | Weinrib |
| 4,723,549 A | 2/1988 | Wholey et al. |
| 4,727,873 A | 3/1988 | Mobin-Uddin |
| 4,781,177 A | 11/1988 | Lebigot |
| 4,790,812 A | 12/1988 | Hawkins, Jr. et al. |
| 4,790,813 A | 12/1988 | Kensey |
| 4,794,928 A | 1/1989 | Kletschka |
| 4,832,055 A | 5/1989 | Palestrant |
| 4,873,978 A | 10/1989 | Ginsburg |
| 4,921,478 A | 5/1990 | Solano et al. |
| 4,921,484 A | 5/1990 | Hillstead |
| 4,969,891 A | 11/1990 | Gewertz |
| 4,990,156 A | 2/1991 | Lefebvre |
| 4,997,435 A | 3/1991 | Demeter |
| 4,998,539 A | 3/1991 | Delsanti |
| 5,053,008 A | 10/1991 | Bajaj |
| 5,064,428 A | 11/1991 | Cope et al. |
| 5,071,407 A | 12/1991 | Termin et al. |
| 5,092,839 A | 3/1992 | Kipperman |
| 5,100,423 A | 3/1992 | Fearnot |
| 5,100,425 A | 3/1992 | Fischell et al. |
| 5,102,415 A | 4/1992 | Guenther et al. |
| 5,108,419 A | 4/1992 | Reger et al. |
| 5,152,777 A | 10/1992 | Goldberg et al. |
| 5,158,548 A | 10/1992 | Lau |
| 5,160,342 A | 11/1992 | Reger et al. |
| 5,192,286 A | 3/1993 | Phan et al. |
| 5,324,304 A | 6/1994 | Rasmussen |
| 5,329,942 A | 7/1994 | Gunther et al. |
| 5,330,482 A | 7/1994 | Gibbs et al. |
| 5,350,398 A | 9/1994 | Pavcnik et al. |
| 5,370,657 A | 12/1994 | Irie |
| 5,375,612 A | 12/1994 | Cottenceau et al. |
| 5,383,887 A | 1/1995 | Nadal |
| 5,421,832 A | 6/1995 | Lefebvre |
| 5,490,859 A | 2/1996 | Mische et al. |
| 5,496,277 A | 3/1996 | Termin et al. |
| 5,496,330 A | 3/1996 | Bates et al. |
| 5,501,694 A | 3/1996 | Ressemann et al. |
| 5,549,626 A | 8/1996 | Miller et al. |
| 5,601,595 A | 2/1997 | Smith |
| 5,626,605 A | 5/1997 | Irie et al. |
| 5,634,942 A | 6/1997 | Chevillon et al. |
| 5,649,953 A | 7/1997 | Lefebvre |
| 5,658,296 A | 8/1997 | Bates et al. |
| 5,662,671 A | 9/1997 | Barbut et al. |
| 5,669,933 A | 9/1997 | Simon et al. |
| 5,681,347 A | 10/1997 | Cathcart et al. |
| 5,695,518 A | 12/1997 | Laerum |
| 5,695,519 A | 12/1997 | Summers et al. |
| 5,720,764 A | 2/1998 | Naderlinger |
| 5,725,550 A | 3/1998 | Nadal |
| 5,746,767 A | 5/1998 | Smith |
| 5,755,790 A | 5/1998 | Chevillon et al. |
| 5,769,816 A | 6/1998 | Barbut et al. |
| 5,772,674 A | 6/1998 | Nakhjavan |
| 5,776,162 A | 7/1998 | Kleshinski |
| 5,779,716 A | 7/1998 | Cano et al. |
| 5,792,145 A | 8/1998 | Bates et al. |
| 5,792,156 A | 8/1998 | Perouse |
| 5,792,157 A | 8/1998 | Mische et al. |
| 5,795,322 A | 8/1998 | Boudewijn |
| 5,800,457 A | 9/1998 | Gelbfish |
| 5,800,525 A | 9/1998 | Bachinski et al. |
| 5,810,874 A | 9/1998 | Lefebvre |
| 5,814,064 A | 9/1998 | Daniel et al. |
| 5,827,324 A | 10/1998 | Cassell et al. |
| 5,833,650 A | 11/1998 | Imran |
| 5,836,868 A | 11/1998 | Ressemann et al. |
| 5,846,251 A | 12/1998 | Hart |
| 5,846,260 A | 12/1998 | Maas |
| 5,848,964 A | 12/1998 | Samuels |
| 5,868,708 A | 2/1999 | Hart et al. |
| 5,876,367 A | 3/1999 | Kaganov et al. |
| 5,897,567 A | 4/1999 | Ressemann et al. |
| 5,910,154 A | 6/1999 | Tsugita et al. |
| 5,911,734 A | 6/1999 | Tsugita et al. |
| 5,935,139 A | 8/1999 | Bates |
| 5,941,869 A | 8/1999 | Patterson et al. |
| 5,941,896 A | 8/1999 | Kerr |
| 5,944,728 A | 8/1999 | Bates |
| 5,954,745 A | 9/1999 | Gertler et al. |
| 5,968,071 A | 10/1999 | Chevillon et al. |
| 5,976,172 A | 11/1999 | Homsma et al. |
| 5,980,555 A | 11/1999 | Barbut et al. |
| 5,989,281 A | 11/1999 | Barbut et al. |
| 6,001,118 A | 12/1999 | Daniel et al. |
| 6,007,557 A | 12/1999 | Ambrisco et al. |
| 6,013,093 A | 1/2000 | Nott et al. |
| 6,022,336 A | 2/2000 | Zadno-Azizi et al. |
| 6,027,520 A | 2/2000 | Tsugita et al. |
| 6,042,598 A | 3/2000 | Tsugita et al. |
| 6,051,015 A | 4/2000 | Maahs |
| 6,053,932 A | 4/2000 | Daniel et al. |
| 6,059,814 A | 5/2000 | Ladd |
| 6,066,158 A | 5/2000 | Engelson et al. |
| 6,074,357 A | 6/2000 | Kaganov et al. |
| 6,086,605 A | 7/2000 | Barbut et al. |
| 6,090,097 A | 7/2000 | Barbut et al. |
| 6,096,053 A | 8/2000 | Bates |
| 6,099,534 A | 8/2000 | Bates et al. |
| 6,099,549 A | 8/2000 | Bosma et al. |
| 6,117,154 A | 9/2000 | Barbut et al. |
| 6,129,739 A | 10/2000 | Khosravi |
| 6,136,015 A | 10/2000 | Kurz et al. |
| 6,136,016 A | 10/2000 | Barbut et al. |
| 6,142,987 A | 11/2000 | Tsugita |
| 6,152,946 A | 11/2000 | Broome et al. |
| 6,152,947 A | 11/2000 | Ambrisco et al. |
| 6,165,198 A | 12/2000 | McGurk et al. |
| 6,165,200 A | 12/2000 | Tsugita et al. |
| 6,168,579 B1 | 1/2001 | Tsugita et al. |
| 6,168,604 B1 | 1/2001 | Cano |
| 6,171,327 B1 | 1/2001 | Daniel et al. |
| 6,171,328 B1 | 1/2001 | Addis |
| 6,174,318 B1 | 1/2001 | Bates et al. |
| 6,176,849 B1 | 1/2001 | Yang et al. |
| 6,179,859 B1 | 1/2001 | Bates et al. |
| 6,179,860 B1 | 1/2001 | Fulton, III et al. |
| 6,179,861 B1 | 1/2001 | Khosravi et al. |
| 6,187,025 B1 | 2/2001 | Machek |
| 6,203,561 B1 | 3/2001 | Ramee et al. |
| 6,206,868 B1 | 3/2001 | Parodi |
| 6,214,026 B1 | 4/2001 | Lepak et al. |
| 6,224,620 B1 | 5/2001 | Maahs |
| 6,235,044 B1 | 5/2001 | Root et al. |
| 6,235,045 B1 | 5/2001 | Barbut et al. |
| 6,238,412 B1 | 5/2001 | Dubrul et al. |
| 6,241,746 B1 | 6/2001 | Bosma et al. |
| 6,245,012 B1 | 6/2001 | Kleshinski |
| 6,245,087 B1 | 6/2001 | Addis |
| 6,245,088 B1 | 6/2001 | Lowery |
| 6,245,089 B1 | 6/2001 | Daniel et al. |
| 6,251,122 B1 | 6/2001 | Tsukernik |
| 6,254,633 B1 | 7/2001 | Pinchuk et al. |
| 6,258,115 B1 | 7/2001 | Dubrul |
| 6,258,120 B1 | 7/2001 | McKenzie et al. |
| 6,264,663 B1 | 7/2001 | Cano |
| 6,264,672 B1 | 7/2001 | Fisher |
| 6,267,776 B1 | 7/2001 | O'Connell |
| 6,267,777 B1 | 7/2001 | Bosma et al. |
| 6,270,477 B1 | 8/2001 | Bagaoisan |
| 6,270,513 B1 | 8/2001 | Tsugita et al. |

| Patent No. | Date | Inventor(s) | Patent No. | Date | Inventor(s) |
|---|---|---|---|---|---|
| 6,273,901 B1 | 8/2001 | Whitcher et al. | 6,530,940 B2 | 3/2003 | Fisher |
| 6,277,138 B1 | 8/2001 | Levinson et al. | 6,533,800 B1 | 3/2003 | Barbut |
| 6,277,139 B1 | 8/2001 | Levinson et al. | 6,537,294 B1 | 3/2003 | Boyle et al. |
| 6,280,451 B1 | 8/2001 | Bates et al. | 6,537,295 B2 | 3/2003 | Peterson |
| 6,287,321 B1 | 9/2001 | Jang | 6,537,296 B2 | 3/2003 | Levinson et al. |
| 6,290,656 B1 | 9/2001 | Boyle et al. | 6,537,297 B2 | 3/2003 | Tsugita et al. |
| 6,290,710 B1 | 9/2001 | Cryer et al. | 6,540,722 B1 | 4/2003 | Boyle et al. |
| 6,295,989 B1 | 10/2001 | Connors, III | 6,540,767 B1 | 4/2003 | Walak et al. |
| 6,306,163 B1 | 10/2001 | Fitz | 6,540,768 B1 | 4/2003 | Diaz et al. |
| 6,319,242 B1 | 11/2001 | Patterson et al. | 6,544,276 B1 | 4/2003 | Azizi |
| 6,319,268 B1 | 11/2001 | Ambrisco et al. | 6,544,279 B1 | 4/2003 | Hopkins et al. |
| 6,325,815 B1 | 12/2001 | Kusleika et al. | 6,544,280 B1 | 4/2003 | Daniel et al. |
| 6,336,934 B1 | 1/2002 | Gilson et al. | 6,547,759 B1 | 4/2003 | Fisher |
| 6,340,364 B2 | 1/2002 | Kanesaka | 6,551,268 B1 | 4/2003 | Kaganov et al. |
| 6,340,465 B1 | 1/2002 | Hsu et al. | 6,551,341 B2 | 4/2003 | Boylan et al. |
| 6,346,116 B1 | 2/2002 | Brooks et al. | 6,551,342 B1 | 4/2003 | Shen et al. |
| 6,348,056 B1 | 2/2002 | Bates et al. | 6,558,401 B1 | 5/2003 | Azizi |
| 6,355,051 B1 | 3/2002 | Sisskind et al. | 6,558,405 B1 | 5/2003 | McInnes |
| 6,361,545 B1 | 3/2002 | Macoviak et al. | 6,562,058 B2 | 5/2003 | Seguin |
| 6,361,546 B1 | 3/2002 | Khosravi | 6,565,591 B2 | 5/2003 | Kelly et al. |
| 6,364,895 B1 | 4/2002 | Greenhalgh | 6,569,184 B2 | 5/2003 | Huter |
| 6,364,896 B1 | 4/2002 | Addis | 6,575,995 B1 | 6/2003 | Huter et al. |
| 6,371,969 B1 | 4/2002 | Tsugita et al. | 6,575,996 B1 | 6/2003 | Denison et al. |
| 6,371,970 B1 | 4/2002 | Khosravi et al. | 6,575,997 B1 | 6/2003 | Palmer et al. |
| 6,371,971 B1 | 4/2002 | Tsugita et al. | 6,582,447 B1 | 6/2003 | Patel et al. |
| 6,375,670 B1 | 4/2002 | Greenhalgh | 6,582,448 B1 | 6/2003 | Boyle et al. |
| 6,383,206 B1 | 5/2002 | Gillick et al. | 6,585,756 B1 | 7/2003 | Strecker |
| 6,384,062 B1 | 5/2002 | Ikeda et al. | 6,589,263 B1 | 7/2003 | Hopkins et al. |
| 6,391,044 B1 | 5/2002 | Yadav et al. | 6,589,265 B1 | 7/2003 | Palmer et al. |
| 6,394,978 B1 | 5/2002 | Boyle et al. | 6,592,546 B1 | 7/2003 | Barbut et al. |
| 6,395,014 B1 | 5/2002 | Macoviak et al. | 6,592,606 B2 | 7/2003 | Huter et al. |
| 6,398,756 B2 | 6/2002 | Peterson et al. | 6,592,607 B1 | 7/2003 | Palmer et al. |
| 6,402,771 B1 | 6/2002 | Palmer et al. | 6,592,616 B1 | 7/2003 | Stack et al. |
| 6,406,471 B1 | 6/2002 | Jang et al. | 6,596,011 B2 | 7/2003 | Johnson et al. |
| 6,423,032 B2 | 7/2002 | Parodi | 6,599,307 B1 | 7/2003 | Huter et al. |
| 6,423,086 B1 | 7/2002 | Barbut et al. | 6,599,308 B2 | 7/2003 | Amplatz |
| 6,425,909 B1 | 7/2002 | Dieck et al. | 6,602,269 B2 | 8/2003 | Wallace et al. |
| 6,428,559 B1 | 8/2002 | Johnson | 6,602,271 B2 | 8/2003 | Adams et al. |
| 6,432,122 B1 | 8/2002 | Gilson et al. | 6,602,272 B2 | 8/2003 | Boylan et al. |
| 6,436,121 B1 | 8/2002 | Blom | 6,602,273 B2 | 8/2003 | Marshall |
| 6,443,926 B1 | 9/2002 | Kletschka | 6,605,102 B1 | 8/2003 | Mazzocchi et al. |
| 6,443,971 B1 | 9/2002 | Boylan et al. | 6,605,111 B2 | 8/2003 | Bose et al. |
| 6,443,972 B1 | 9/2002 | Bosma | 6,607,506 B2 | 8/2003 | Kletschka |
| 6,443,979 B1 | 9/2002 | Stalker et al. | 6,610,077 B1 | 8/2003 | Hancock et al. |
| 6,447,530 B1 | 9/2002 | Ostrovsky et al. | 6,616,679 B1 | 9/2003 | Khosravi et al. |
| 6,447,531 B1 | 9/2002 | Amplatz | 6,616,680 B1 | 9/2003 | Thielen |
| 6,450,989 B2 | 9/2002 | Dubrul et al. | 6,616,681 B2 | 9/2003 | Hanson et al. |
| 6,458,139 B1 | 10/2002 | Palmer et al. | 6,616,682 B2 | 9/2003 | Joergensen et al. |
| 6,461,370 B1 | 10/2002 | Gray et al. | 6,620,148 B1 | 9/2003 | Tsugita et al. |
| 6,468,291 B2 | 10/2002 | Bates et al. | 6,620,182 B1 | 9/2003 | Khosravi |
| 6,482,222 B1 | 11/2002 | Bruckheimer et al. | 6,623,450 B1 | 9/2003 | Dutta |
| 6,485,456 B1 | 11/2002 | Kletschka | 6,629,953 B1 | 10/2003 | Boyd |
| 6,485,497 B2 | 11/2002 | Wensel et al. | 6,632,236 B2 | 10/2003 | Hogendijk |
| 6,485,500 B1 | 11/2002 | Kokish et al. | 6,632,241 B1 | 10/2003 | Hancock et al. |
| 6,485,501 B1 | 11/2002 | Green | 6,635,068 B1 | 10/2003 | Dubrul et al. |
| 6,485,502 B2 | 11/2002 | Don Michael et al. | 6,635,070 B2 | 10/2003 | Leeflang et al. |
| 6,485,507 B1 | 11/2002 | Walak et al. | 6,638,293 B1 | 10/2003 | Makower et al. |
| 6,494,895 B2 | 12/2002 | Addis | 6,638,294 B1 | 10/2003 | Palmer |
| 6,499,487 B1 | 12/2002 | McKenzie et al. | 6,645,220 B1 | 11/2003 | Huter et al. |
| 6,500,166 B1 | 12/2002 | Zadno Azizi et al. | 6,645,221 B1 | 11/2003 | Richter |
| 6,506,203 B1 | 1/2003 | Boyle et al. | 6,645,223 B2 | 11/2003 | Boyle et al. |
| 6,506,205 B2 | 1/2003 | Goldberg et al. | 6,645,224 B2 | 11/2003 | Gilson et al. |
| 6,511,492 B1 | 1/2003 | Rosenbluth | 6,652,480 B1 | 11/2003 | Imran et al. |
| 6,511,496 B1 | 1/2003 | Huter et al. | 6,652,505 B1 | 11/2003 | Tsugita et al. |
| 6,511,497 B1 | 1/2003 | Braun et al. | 6,652,554 B1 | 11/2003 | Wholey et al. |
| 6,511,503 B1 | 1/2003 | Burkett et al. | 6,652,557 B1 | 11/2003 | MacDonald |
| 6,514,273 B1 | 2/2003 | Voss et al. | 6,656,202 B2 | 12/2003 | Papp et al. |
| 6,517,550 B1 | 2/2003 | Konya et al. | 6,656,203 B2 | 12/2003 | Roth et al. |
| 6,517,559 B1 | 2/2003 | O'Connell | 6,656,204 B2 | 12/2003 | Ambrisco et al. |
| 6,520,978 B1 | 2/2003 | Blackledge et al. | 6,656,351 B2 | 12/2003 | Boyle |
| 6,527,746 B1 | 3/2003 | Oslund et al. | 6,660,021 B1 | 12/2003 | Palmer et al. |
| 6,527,791 B2 | 3/2003 | Fisher | 6,663,650 B2 | 12/2003 | Sepetka et al. |
| 6,530,939 B1 | 3/2003 | Hopkins et al. | 6,663,651 B2 | 12/2003 | Krolik et al. |

| Patent No. | Date | Inventor |
|---|---|---|
| 6,663,652 B2 | 12/2003 | Daniel et al. |
| 6,673,090 B2 | 1/2004 | Root et al. |
| 6,676,666 B2 | 1/2004 | Vrba et al. |
| 6,676,682 B1 | 1/2004 | Tsugita et al. |
| 6,676,683 B1 | 1/2004 | Addis |
| 6,679,902 B1 | 1/2004 | Boyle et al. |
| 6,679,903 B2 | 1/2004 | Kurz |
| 6,682,546 B2 | 1/2004 | Amplatz |
| 6,685,722 B1 | 2/2004 | Rosenbluth et al. |
| 6,689,151 B2 | 2/2004 | Becker et al. |
| 6,692,513 B2 | 2/2004 | Streeter et al. |
| 6,695,813 B1 | 2/2004 | Boyle et al. |
| 6,695,858 B1 | 2/2004 | Dubrul et al. |
| 6,695,864 B2 | 2/2004 | Macoviak et al. |
| 6,696,666 B2 | 2/2004 | Merdan et al. |
| 6,699,260 B2 | 3/2004 | Dubrul et al. |
| 6,702,834 B1 | 3/2004 | Boyle et al. |
| 6,706,055 B2 | 3/2004 | Douk et al. |
| 6,712,834 B2 | 3/2004 | Yassour et al. |
| 6,712,835 B2 | 3/2004 | Mazzocchi et al. |
| 6,716,231 B1 | 4/2004 | Rafiee et al. |
| 6,723,085 B2 | 4/2004 | Jang et al. |
| 6,726,701 B2 | 4/2004 | Gilson |
| 6,726,702 B2 | 4/2004 | Khosravi |
| 6,726,703 B2 | 4/2004 | Broome et al. |
| 6,740,061 B1 | 5/2004 | Oslund et al. |
| 6,743,247 B1 | 6/2004 | Levinson et al. |
| 6,746,469 B2 | 6/2004 | Mouw |
| 6,752,819 B1 | 6/2004 | Brady et al. |
| 6,755,846 B1 | 6/2004 | Yadav |
| 6,758,855 B2 | 7/2004 | Fulton, III et al. |
| 6,761,727 B1 | 7/2004 | Ladd |
| 6,773,448 B2 | 8/2004 | Kusleika et al. |
| 6,790,219 B1 | 9/2004 | Murphy |
| 6,793,666 B2 | 9/2004 | Hansen et al. |
| 6,793,668 B1 | 9/2004 | Fisher |
| 6,800,080 B1 | 10/2004 | Bates |
| 6,814,739 B2 | 11/2004 | Secrest et al. |
| 6,818,006 B2 | 11/2004 | Douk et al. |
| 6,837,898 B2 | 1/2005 | Boyle |
| 6,840,950 B2 | 1/2005 | Stanford et al. |
| 6,843,798 B2 | 1/2005 | Kusleika et al. |
| 6,846,316 B2 | 1/2005 | Abrams |
| 6,846,317 B1 | 1/2005 | Nigon |
| 6,863,696 B2 | 3/2005 | Kantsevitcha et al. |
| 6,866,677 B2 | 3/2005 | Douk et al. |
| 6,872,216 B2 | 3/2005 | Daniel et al. |
| 6,878,151 B2 | 4/2005 | Carrison et al. |
| 6,878,153 B2 | 4/2005 | Linder et al. |
| 6,887,256 B2 | 5/2005 | Gilson et al. |
| 6,887,257 B2 | 5/2005 | Salaheih et al. |
| 6,887,258 B2 | 5/2005 | Denison |
| 6,888,098 B1 | 5/2005 | Merdan et al. |
| 6,890,340 B2 | 5/2005 | Duane |
| 6,890,341 B2 | 5/2005 | Dieck et al. |
| 6,893,450 B2 | 5/2005 | Foster |
| 6,893,451 B2 | 5/2005 | Cano et al. |
| 6,896,690 B1 | 5/2005 | Lambrecht et al. |
| 6,896,691 B2 | 5/2005 | Boylan |
| 6,902,540 B2 | 6/2005 | Dorros et al. |
| 6,908,474 B2 | 6/2005 | Hogenkijk et al. |
| 6,911,036 B2 | 6/2005 | Douk et al. |
| 6,913,612 B2 | 7/2005 | Palmer et al. |
| 6,918,921 B2 | 7/2005 | Brady et al. |
| 6,929,652 B1 | 8/2005 | Andrews |
| 6,932,830 B2 | 8/2005 | Ungs |
| 6,932,831 B2 | 8/2005 | Forber |
| 6,936,058 B2 | 8/2005 | Forde et al. |
| 6,936,059 B2 | 8/2005 | Belef |
| 6,939,361 B1 | 9/2005 | Kleshinski |
| 6,939,362 B2 | 9/2005 | Boyle et al. |
| 6,942,673 B2 | 9/2005 | Bates et al. |
| 6,949,103 B2 | 9/2005 | Mazzocchi et al. |
| 6,951,570 B2 | 10/2005 | Linder et al. |
| 6,953,471 B1 | 10/2005 | Lilly et al. |
| 6,953,472 B2 | 10/2005 | Palmer et al. |
| 6,958,074 B2 | 10/2005 | Russell |
| 6,960,370 B2 | 11/2005 | Monni et al. |
| 6,962,598 B2 | 11/2005 | Linder et al. |
| 6,964,670 B1 | 11/2005 | Shah |
| 6,964,672 B2 | 11/2005 | Brady |
| 6,964,673 B2 | 11/2005 | Tsugita et al. |
| 6,969,395 B2 | 11/2005 | Eskuri |
| 6,969,396 B2 | 11/2005 | Krolik et al. |
| 6,969,402 B2 | 11/2005 | Bales et al. |
| 6,970,730 B2 | 11/2005 | Fuimaono et al. |
| 6,972,025 B2 | 12/2005 | WasDyke |
| 6,973,340 B2 | 12/2005 | Fuimaono et al. |
| 6,974,468 B2 | 12/2005 | DoBrava et al. |
| 6,974,469 B2 | 12/2005 | Broome et al. |
| 6,979,343 B2 | 12/2005 | Russo |
| 6,979,344 B2 | 12/2005 | Jones et al. |
| 6,986,778 B2 | 1/2006 | Zadno-Azizi |
| 6,989,019 B2 | 1/2006 | Mazzocchi |
| 6,989,021 B2 | 1/2006 | Bosma et al. |
| 6,989,027 B2 | 1/2006 | Allen et al. |
| 6,991,641 B2 | 1/2006 | Diaz et al. |
| 6,991,642 B2 | 1/2006 | Petersen |
| RE38,972 E | 2/2006 | Purdy |
| 6,994,718 B2 | 2/2006 | Groothuis et al. |
| 6,997,938 B2 | 2/2006 | Wang et al. |
| 6,997,939 B2 | 2/2006 | Linder et al. |
| 7,001,406 B2 | 2/2006 | Eskuri et al. |
| 7,001,407 B2 | 2/2006 | Hansen et al. |
| 7,004,954 B1 | 2/2006 | Voss et al. |
| 7,004,955 B2 | 2/2006 | Shen et al. |
| 7,004,956 B2 | 2/2006 | Palmer et al. |
| 7,004,964 B2 | 2/2006 | Thompson et al. |
| 7,011,671 B2 | 3/2006 | Welch |
| 7,011,672 B2 | 3/2006 | Barbut et al. |
| 7,014,647 B2 | 3/2006 | Brady et al. |
| 7,018,372 B2 | 3/2006 | Casey |
| 7,018,385 B2 | 3/2006 | Bates et al. |
| 7,018,393 B1 | 3/2006 | Boyle et al. |
| 7,029,440 B2 | 4/2006 | Broome et al. |
| 7,033,375 B2 | 4/2006 | Mazzocchi et al. |
| 7,037,320 B2 | 5/2006 | Brady et al. |
| 7,041,116 B2 | 5/2006 | Goto et al. |
| 7,044,958 B2 | 5/2006 | Douk et al. |
| 7,048,752 B2 | 5/2006 | Mazzocchi |
| 7,048,758 B2 | 5/2006 | Boyle et al. |
| 7,056,328 B2 | 6/2006 | Arnott |
| 7,060,082 B2 | 6/2006 | Goll et al. |
| 7,077,854 B2 | 7/2006 | Khosravi |
| 7,094,243 B2 | 8/2006 | Mulholland |
| 7,094,249 B1 | 8/2006 | Broome et al. |
| 7,097,440 B2 | 8/2006 | Broome et al. |
| 7,097,651 B2 | 8/2006 | Harrison et al. |
| 7,101,379 B2 | 9/2006 | Gregory, Jr. et al. |
| 7,101,380 B2 | 9/2006 | Khachin et al. |
| 7,108,707 B2 | 9/2006 | Huter et al. |
| 2002/0091408 A1 | 7/2002 | Sutton et al. |
| 2002/0091409 A1 | 7/2002 | Sutton et al. |
| 2002/0095141 A1 | 7/2002 | Belef et al. |
| 2002/0099407 A1 | 7/2002 | Becker et al. |
| 2002/0103501 A1 | 8/2002 | Diaz et al. |
| 2002/0107541 A1 | 8/2002 | Vale et al. |
| 2002/0111648 A1 | 8/2002 | Kusleika et al. |
| 2002/0111649 A1 | 8/2002 | Russo et al. |
| 2002/0115942 A1 | 8/2002 | Stanford et al. |
| 2002/0120286 A1 | 8/2002 | Dobrava et al. |
| 2002/0120287 A1 | 8/2002 | Huter |
| 2002/0121472 A1 | 9/2002 | Garner et al. |
| 2002/0123720 A1 | 9/2002 | Kusleika et al. |
| 2002/0123755 A1 | 9/2002 | Lowe et al. |
| 2002/0128679 A1 | 9/2002 | Turovskiy et al. |

| | | | | | | |
|---|---|---|---|---|---|---|
| 2002/0128680 A1 | 9/2002 | Pavlovic | | 2003/0144688 A1* | 7/2003 | Brady et al. .................. 606/200 |
| 2002/0128681 A1 | 9/2002 | Broome et al. | | 2003/0144689 A1* | 7/2003 | Brady et al. .................. 606/200 |
| 2002/0133092 A1 | 9/2002 | Oslund et al. | | 2003/0150821 A1 | 8/2003 | Bates et al. |
| 2002/0138094 A1 | 9/2002 | Borillo et al. | | 2003/0153935 A1 | 8/2003 | Mialhe |
| 2002/0138095 A1 | 9/2002 | Mazzocchi et al. | | 2003/0153942 A1 | 8/2003 | Wang et al. |
| 2002/0143360 A1 | 10/2002 | Douk et al. | | 2003/0153943 A1 | 8/2003 | Michael et al. |
| 2002/0143361 A1 | 10/2002 | Douk et al. | | 2003/0158574 A1 | 8/2003 | Esch et al. |
| 2002/0151927 A1 | 10/2002 | Douk et al. | | 2003/0163064 A1 | 8/2003 | Vrba et al. |
| 2002/0156456 A1 | 10/2002 | Fisher | | 2003/0171644 A1 | 9/2003 | Anderson et al. |
| 2002/0156457 A1 | 10/2002 | Fisher | | 2003/0171770 A1 | 9/2003 | Kusleika et al. |
| 2002/0161390 A1 | 10/2002 | Mouw | | 2003/0171771 A1 | 9/2003 | Anderson et al. |
| 2002/0161392 A1 | 10/2002 | Dubrul | | 2003/0171803 A1 | 9/2003 | Shimon |
| 2002/0161393 A1 | 10/2002 | Demond et al. | | 2003/0176884 A1 | 9/2003 | Berrada et al. |
| 2002/0161395 A1 | 10/2002 | Douk et al. | | 2003/0176885 A1 | 9/2003 | Broome et al. |
| 2002/0165576 A1 | 11/2002 | Boyle et al. | | 2003/0176886 A1 | 9/2003 | Wholey et al. |
| 2002/0169414 A1 | 11/2002 | Kletschka | | 2003/0176889 A1 | 9/2003 | Boyle et al. |
| 2002/0169458 A1 | 11/2002 | Connors, III | | 2003/0181943 A1 | 9/2003 | Daniel et al. |
| 2002/0169472 A1 | 11/2002 | Douk et al. | | 2003/0187474 A1 | 10/2003 | Keegan et al. |
| 2002/0169474 A1 | 11/2002 | Kusleika et al. | | 2003/0187475 A1 | 10/2003 | Tsugita et al. |
| 2002/0173815 A1 | 11/2002 | Hogendijk et al. | | 2003/0187495 A1 | 10/2003 | Cully et al. |
| 2002/0173817 A1 | 11/2002 | Kletschka et al. | | 2003/0191493 A1 | 10/2003 | Epstein et al. |
| 2002/0188313 A1 | 12/2002 | Johnson et al. | | 2003/0195554 A1 | 10/2003 | Shen et al. |
| 2002/0188314 A1 | 12/2002 | Anderson et al. | | 2003/0195555 A1 | 10/2003 | Khairkhahan et al. |
| 2002/0193825 A1 | 12/2002 | McGuckin et al. | | 2003/0195556 A1 | 10/2003 | Stack et al. |
| 2002/0193826 A1 | 12/2002 | McGuckin et al. | | 2003/0199819 A1 | 10/2003 | Beck |
| 2002/0193827 A1 | 12/2002 | McGuckin et al. | | 2003/0199921 A1 | 10/2003 | Palmer et al. |
| 2002/0193828 A1 | 12/2002 | Griffin et al. | | 2003/0204168 A1 | 10/2003 | Bosma et al. |
| 2003/0004536 A1 | 1/2003 | Boylan et al. | | 2003/0204202 A1 | 10/2003 | Palmer et al. |
| 2003/0004537 A1 | 1/2003 | Boyle et al. | | 2003/0208222 A1 | 11/2003 | Zadno-Azizi |
| 2003/0004539 A1 | 1/2003 | Linder et al. | | 2003/0208224 A1 | 11/2003 | Broome |
| 2003/0004540 A1 | 1/2003 | Linder et al. | | 2003/0208225 A1 | 11/2003 | Goll et al. |
| 2003/0004541 A1 | 1/2003 | Linder et al. | | 2003/0208226 A1 | 11/2003 | Bruckheimer et al. |
| 2003/0009188 A1 | 1/2003 | Linder et al. | | 2003/0208227 A1 | 11/2003 | Thomas |
| 2003/0009189 A1 | 1/2003 | Gilson et al. | | 2003/0208228 A1 | 11/2003 | Gilson et al. |
| 2003/0010686 A1 | 1/2003 | Sawada et al. | | 2003/0208229 A1 | 11/2003 | Kletschka |
| 2003/0015206 A1 | 1/2003 | Roth et al. | | 2003/0212361 A1 | 11/2003 | Boyle et al. |
| 2003/0018354 A1 | 1/2003 | Roth et al. | | 2003/0212429 A1 | 11/2003 | Keegan et al. |
| 2003/0023265 A1 | 1/2003 | Forber | | 2003/0212431 A1 | 11/2003 | Brady et al. |
| 2003/0028238 A1 | 2/2003 | Burkett et al. | | 2003/0212434 A1 | 11/2003 | Thielen |
| 2003/0032941 A1 | 2/2003 | Boyle et al. | | 2003/0216774 A1 | 11/2003 | Larson |
| 2003/0032977 A1 | 2/2003 | Brady et al. | | 2003/0220665 A1 | 11/2003 | Eskuri et al. |
| 2003/0040772 A1 | 2/2003 | Hyodoh et al. | | 2003/0225418 A1 | 12/2003 | Esksuri et al. |
| 2003/0042186 A1 | 3/2003 | Boyle et al. | | 2003/0225435 A1 | 12/2003 | Huter et al. |
| 2003/0045898 A1 | 3/2003 | Harrison et al. | | 2003/0229295 A1 | 12/2003 | Houde et al. |
| 2003/0057156 A1 | 3/2003 | Peterson et al. | | 2003/0229374 A1 | 12/2003 | Brady et al. |
| 2003/0060782 A1 | 3/2003 | Bose et al. | | 2003/0233117 A1 | 12/2003 | Adams et al. |
| 2003/0060843 A1 | 3/2003 | Boucher | | 2003/0236545 A1 | 12/2003 | Gilson |
| 2003/0060844 A1 | 3/2003 | Borillo et al. | | 2004/0002730 A1 | 1/2004 | Denison et al. |
| 2003/0065354 A1 | 4/2003 | Boyle et al. | | 2004/0006361 A1 | 1/2004 | Boyle et al. |
| 2003/0069596 A1 | 4/2003 | Eskuri | | 2004/0006364 A1 | 1/2004 | Ladd |
| 2003/0069597 A1 | 4/2003 | Petersen | | 2004/0006365 A1 | 1/2004 | Brady et al. |
| 2003/0078519 A1 | 4/2003 | Salahieh et al. | | 2004/0006366 A1 | 1/2004 | Huter et al. |
| 2003/0078614 A1 | 4/2003 | Satahieh et al. | | 2004/0006367 A1 | 1/2004 | Johnson et al. |
| 2003/0083692 A1 | 5/2003 | Vrba et al. | | 2004/0006368 A1 | 1/2004 | Mazzocchi et al. |
| 2003/0083693 A1 | 5/2003 | Daniel et al. | | 2004/0015184 A1 | 1/2004 | Boyle et al. |
| 2003/0100917 A1 | 5/2003 | Boyle et al. | | 2004/0019363 A1 | 1/2004 | Hanson et al. |
| 2003/0100918 A1 | 5/2003 | Duane | | 2004/0034385 A1 | 2/2004 | Gilson et al. |
| 2003/0105484 A1 | 6/2003 | Boyle et al. | | 2004/0039411 A1 | 2/2004 | Gilson et al. |
| 2003/0109824 A1 | 6/2003 | Anderson et al. | | 2004/0044359 A1 | 3/2004 | Renati et al. |
| 2003/0114879 A1 | 6/2003 | Euteneuer et al. | | 2004/0044360 A1 | 3/2004 | Lowe |
| 2003/0114880 A1 | 6/2003 | Hansen et al. | | 2004/0049226 A1 | 3/2004 | Keegan et al. |
| 2003/0120303 A1 | 6/2003 | Boyle et al. | | 2004/0059372 A1 | 3/2004 | Tsugita |
| 2003/0130680 A1 | 7/2003 | Russell | | 2004/0059373 A1 | 3/2004 | Shapiro et al. |
| 2003/0130681 A1 | 7/2003 | Ungs | | 2004/0082967 A1 | 4/2004 | Broome et al. |
| 2003/0130682 A1 | 7/2003 | Broome et al. | | 2004/0082968 A1 | 4/2004 | Krolik et al. |
| 2003/0130684 A1 | 7/2003 | Brady et al. | | 2004/0088000 A1 | 5/2004 | Muller |
| 2003/0130685 A1 | 7/2003 | Daniel et al. | | 2004/0088002 A1 | 5/2004 | Boyle et al. |
| 2003/0130687 A1 | 7/2003 | Daniel et al. | | 2004/0093009 A1 | 5/2004 | Denison et al. |
| 2003/0130688 A1 | 7/2003 | Daniel et al. | | 2004/0093010 A1 | 5/2004 | Gesswein et al. |
| 2003/0135162 A1 | 7/2003 | Deyette, Jr. et al. | | 2004/0093011 A1 | 5/2004 | Vrba |
| 2003/0135232 A1 | 7/2003 | Douk et al. | | 2004/0093012 A1 | 5/2004 | Cully et al. |
| 2003/0139764 A1 | 7/2003 | Levinson et al. | | 2004/0093013 A1 | 5/2004 | Brady et al. |
| 2003/0144685 A1 | 7/2003 | Boyle et al. | | 2004/0098022 A1 | 5/2004 | Barone |

| | | | | | |
|---|---|---|---|---|---|
| 2004/0098026 A1 | 5/2004 | Joergensen et al. | 2005/0113865 A1 | 5/2005 | Daniel et al. |
| 2004/0098032 A1 | 5/2004 | Papp et al. | 2005/0119688 A1 | 6/2005 | Bergheim |
| 2004/0098033 A1 | 5/2004 | Leeflang et al. | 2005/0119689 A1 | 6/2005 | Mazzocchi et al. |
| 2004/0102806 A1 | 5/2004 | Broome et al. | 2005/0119690 A1 | 6/2005 | Mazzocchi et al. |
| 2004/0102807 A1 | 5/2004 | Kusleika et al. | 2005/0119691 A1 | 6/2005 | Daniel et al. |
| 2004/0106944 A1 | 6/2004 | Daniel et al. | 2005/0124931 A1 | 6/2005 | Fulton et al. |
| 2004/0111111 A1 | 6/2004 | Lin | 2005/0125023 A1 | 6/2005 | Bates et al. |
| 2004/0116960 A1 | 6/2004 | Demond et al. | 2005/0131450 A1 | 6/2005 | Nicholson et al. |
| 2004/0122466 A1 | 6/2004 | Bales | 2005/0131453 A1 | 6/2005 | Parodi |
| 2004/0127933 A1 | 7/2004 | Demond et al. | 2005/0149110 A1 | 7/2005 | Wholey et al. |
| 2004/0127934 A1 | 7/2004 | Gilson et al. | 2005/0149112 A1 | 7/2005 | Barbut |
| 2004/0127936 A1 | 7/2004 | Salahieh et al. | 2005/0149113 A1 | 7/2005 | Douk et al. |
| 2004/0138693 A1 | 7/2004 | Eskuri et al. | 2005/0159772 A1 | 7/2005 | Lowe et al. |
| 2004/0138694 A1 | 7/2004 | Tran et al. | 2005/0159773 A1 | 7/2005 | Broome et al. |
| 2004/0138696 A1 | 7/2004 | Drasler et al. | 2005/0159774 A1 | 7/2005 | Belef |
| 2004/0147955 A1 | 7/2004 | Beulke et al. | 2005/0171573 A1 | 8/2005 | Salahieh et al. |
| 2004/0153118 A1 | 8/2004 | Clubb et al. | 2005/0177187 A1 | 8/2005 | Gray et al. |
| 2004/0153119 A1 | 8/2004 | Kusleika et al. | 2005/0182440 A1 | 8/2005 | Bates et al. |
| 2004/0158275 A1 | 8/2004 | Crank et al. | 2005/0182441 A1 | 8/2005 | Denison et al. |
| 2004/0158277 A1 | 8/2004 | Lowe et al. | 2005/0192623 A1 | 9/2005 | Mazzocchi et al. |
| 2004/0158278 A1 | 8/2004 | Becker et al. | 2005/0192624 A1 | 9/2005 | Mazzocchi et al. |
| 2004/0158279 A1 | 8/2004 | Petersen | 2005/0203567 A1 | 9/2005 | Linder et al. |
| 2004/0158280 A1 | 8/2004 | Morris et al. | 2005/0203568 A1 | 9/2005 | Burg et al. |
| 2004/0158281 A1 | 8/2004 | Boylan et al. | 2005/0203569 A1 | 9/2005 | Kusleika et al. |
| 2004/0167564 A1 | 8/2004 | Fedie | 2005/0203570 A1 | 9/2005 | Mazzocchi et al. |
| 2004/0167565 A1 | 8/2004 | Beulke et al. | 2005/0203571 A1 | 9/2005 | Mazzocchi et al. |
| 2004/0167566 A1 | 8/2004 | Beulke et al. | 2005/0209634 A1 | 9/2005 | Brady et al. |
| 2004/0167567 A1 | 8/2004 | Cano et al. | 2005/0209635 A1 | 9/2005 | Gilson et al. |
| 2004/0167568 A1 | 8/2004 | Boylan et al. | 2005/0216051 A1 | 9/2005 | Mazzocchi et al. |
| 2004/0172055 A1 | 9/2004 | Huter et al. | 2005/0216052 A1 | 9/2005 | Mazzocchi et al. |
| 2004/0176794 A1 | 9/2004 | Khosravi | 2005/0216053 A1 | 9/2005 | Douk et al. |
| 2004/0193207 A1* | 9/2004 | Boismier .................... 606/200 | 2005/0222583 A1 | 10/2005 | Cano et al. |
| 2004/0193208 A1 | 9/2004 | Talpade et al. | 2005/0222604 A1 | 10/2005 | Schaeffer et al. |
| 2004/0199198 A1 | 10/2004 | Beulke et al. | 2005/0222607 A1 | 10/2005 | Palmer et al. |
| 2004/0199199 A1 | 10/2004 | Krolik et al. | 2005/0228437 A1 | 10/2005 | Gilson et al. |
| 2004/0199203 A1 | 10/2004 | Oslund et al. | 2005/0228438 A1 | 10/2005 | Sachar et al. |
| 2004/0204737 A1 | 10/2004 | Boismier et al. | 2005/0228439 A1 | 10/2005 | Andrews et al. |
| 2004/0210250 A1 | 10/2004 | Eskuri | 2005/0234502 A1 | 10/2005 | Gilson et al. |
| 2004/0220608 A1 | 11/2004 | D'Aquanni et al. | 2005/0240215 A1 | 10/2005 | Ellis |
| 2004/0220609 A1 | 11/2004 | Douk et al. | 2005/0245866 A1 | 11/2005 | Azizi |
| 2004/0220611 A1 | 11/2004 | Ogle | 2005/0267517 A1 | 12/2005 | Ungs |
| 2004/0225322 A1 | 11/2004 | Garrison et al. | 2005/0283184 A1 | 12/2005 | Gilson et al. |
| 2004/0236368 A1 | 11/2004 | McGucklin, Jr. et al. | 2005/0283185 A1 | 12/2005 | Linder et al. |
| 2004/0236369 A1 | 11/2004 | Dubrul | 2005/0283186 A1 | 12/2005 | Berrada et al. |
| 2004/0249409 A1 | 12/2004 | Krolik et al. | 2005/0288705 A1 | 12/2005 | Gilson et al. |
| 2004/0254601 A1 | 12/2004 | Eskuri | 2006/0004403 A1 | 1/2006 | Gilson et al. |
| 2004/0254602 A1 | 12/2004 | Lehe et al. | 2006/0004405 A1 | 1/2006 | Salahieh et al. |
| 2004/0260308 A1 | 12/2004 | Gilson et al. | 2006/0015138 A1 | 1/2006 | Gertner et al. |
| 2004/0260333 A1 | 12/2004 | Dubrul et al. | 2006/0015139 A1 | 1/2006 | Tsugita et al. |
| 2004/0267301 A1 | 12/2004 | Boylan et al. | 2006/0015141 A1 | 1/2006 | Linder et al. |
| 2004/0267302 A1 | 12/2004 | Gilson et al. | 2006/0020285 A1 | 1/2006 | Niermann |
| 2005/0004594 A1 | 1/2005 | Nool et al. | 2006/0020286 A1 | 1/2006 | Niermann |
| 2005/0004595 A1 | 1/2005 | Boyle et al. | 2006/0025803 A1 | 2/2006 | Mitelberg et al. |
| 2005/0004597 A1 | 1/2005 | McGuckin, Jr. et al. | 2006/0025804 A1 | 2/2006 | Krolik et al. |
| 2005/0010245 A1 | 1/2005 | Wasicek | 2006/0025805 A1 | 2/2006 | DoBrava et al. |
| 2005/0010246 A1 | 1/2005 | Streeter et al. | 2006/0030876 A1 | 2/2006 | Peacock, III et al. |
| 2005/0010247 A1 | 1/2005 | Kusleika et al. | 2006/0030877 A1 | 2/2006 | Martinez et al. |
| 2005/0021075 A1 | 1/2005 | Bonnette et al. | 2006/0030878 A1 | 2/2006 | Anderson et al. |
| 2005/0021076 A1 | 1/2005 | Mazzocchi et al. | 2006/0052817 A1 | 3/2006 | Russo et al. |
| 2005/0055048 A1 | 3/2005 | Dieck et al. | 2006/0074446 A1 | 4/2006 | Gilson et al. |
| 2005/0070953 A1 | 3/2005 | Riley | 2006/0095069 A1 | 5/2006 | Shah et al. |
| 2005/0075663 A1 | 4/2005 | Boyle et al. | 2006/0100659 A1 | 5/2006 | Dinh et al. |
| 2005/0080446 A1 | 4/2005 | Gilson et al. | 2006/0100662 A1 | 5/2006 | Daniel et al. |
| 2005/0085842 A1 | 4/2005 | Eversull et al. | 2006/0100663 A1 | 5/2006 | Palmer et al. |
| 2005/0090845 A1 | 4/2005 | Boyd | 2006/0116715 A1 | 6/2006 | Khosravi et al. |
| 2005/0090857 A1 | 4/2005 | Kusleika et al. | 2006/0122643 A1 | 6/2006 | Wasicek |
| 2005/0090858 A1 | 4/2005 | Pavlovic | 2006/0122644 A1 | 6/2006 | Brady et al. |
| 2005/0096691 A1 | 5/2005 | Groothuis et al. | 2006/0122645 A1 | 6/2006 | Brady et al. |
| 2005/0096692 A1 | 5/2005 | Linder et al. | 2006/0129181 A1 | 6/2006 | Callol et al. |
| 2005/0101986 A1 | 5/2005 | Daniel et al. | 2006/0129182 A1 | 6/2006 | Gilson et al. |
| 2005/0101987 A1 | 5/2005 | Salahieh | 2006/0129183 A1 | 6/2006 | Boyle et al. |
| 2005/0101988 A1 | 5/2005 | Stanford et al. | 2006/0149312 A1 | 7/2006 | Arguello et al. |
| 2005/0101989 A1 | 5/2005 | Cully et al. | 2006/0149313 A1 | 7/2006 | Arguello et al. |

| | | | | | |
|---|---|---|---|---|---|
| 2006/0149314 A1 | 7/2006 | Borillo et al. | FR | 2580504 A1 | 10/1986 |
| 2006/0155322 A1 | 7/2006 | Sater et al. | GB | 2020557 | 11/1979 |
| 2006/0161198 A1 | 7/2006 | Sakai et al. | WO | WO92/03097 | 3/1992 |
| 2006/0167491 A1 | 7/2006 | Wholey et al. | WO | WO96/01591 | 1/1996 |
| 2006/0184194 A1 | 8/2006 | Pal et al. | WO | WO97/17100 | 5/1997 |
| 2006/0190025 A1 | 8/2006 | Lehe et al. | WO | WO98/02084 | 1/1998 |
| 2006/0195137 A1 | 8/2006 | Sepetka et al. | WO | WO98/33443 | 8/1998 |
| 2006/0195138 A1 | 8/2006 | Goll et al. | WO | WO 98/39053 | 9/1998 |
| 2006/0200047 A1 | 9/2006 | Galdonik et al. | WO | WO99/23976 | 5/1999 |
| 2006/0200191 A1 | 9/2006 | Zadno-Azizi | WO | WO99/44510 | 9/1999 |
| 2006/0206139 A1 | 9/2006 | Tekulve | WO | WO00/67667 | 11/2000 |
| | | | WO | WO01/10346 | 2/2001 |
| | FOREIGN PATENT DOCUMENTS | | WO | WO01/45592 | 6/2001 |
| | | | WO | WO01/87183 | 11/2001 |
| EP | 0 472 334 A1 | 2/1992 | | | |
| EP | 0533511 A1 | 3/1993 | * cited by examiner | | |

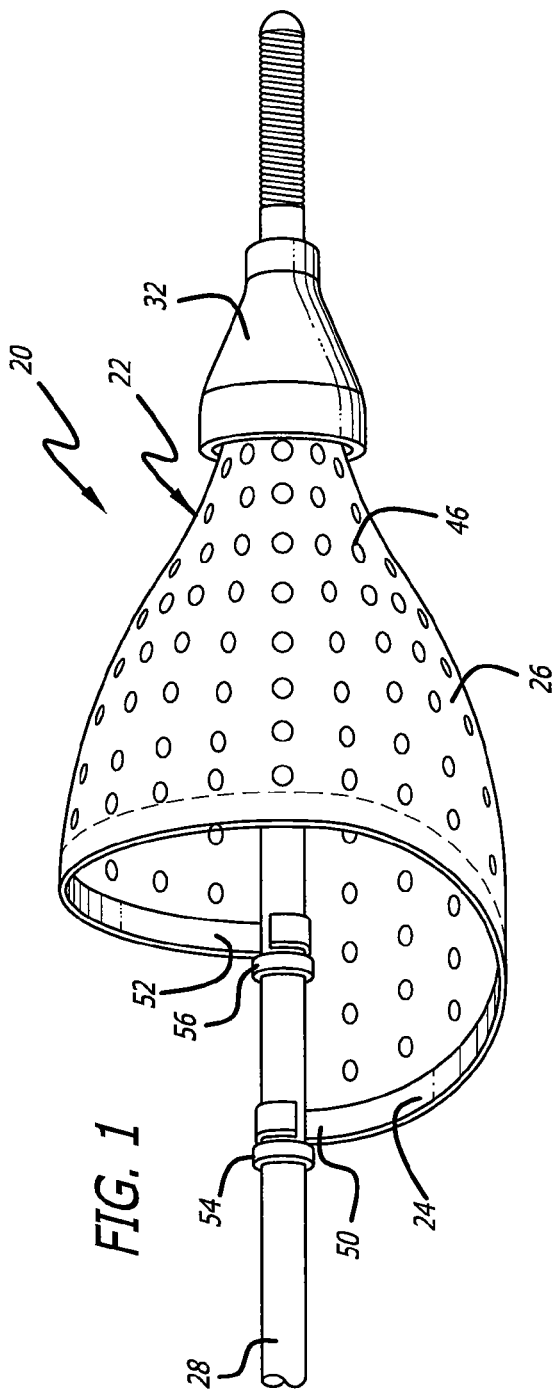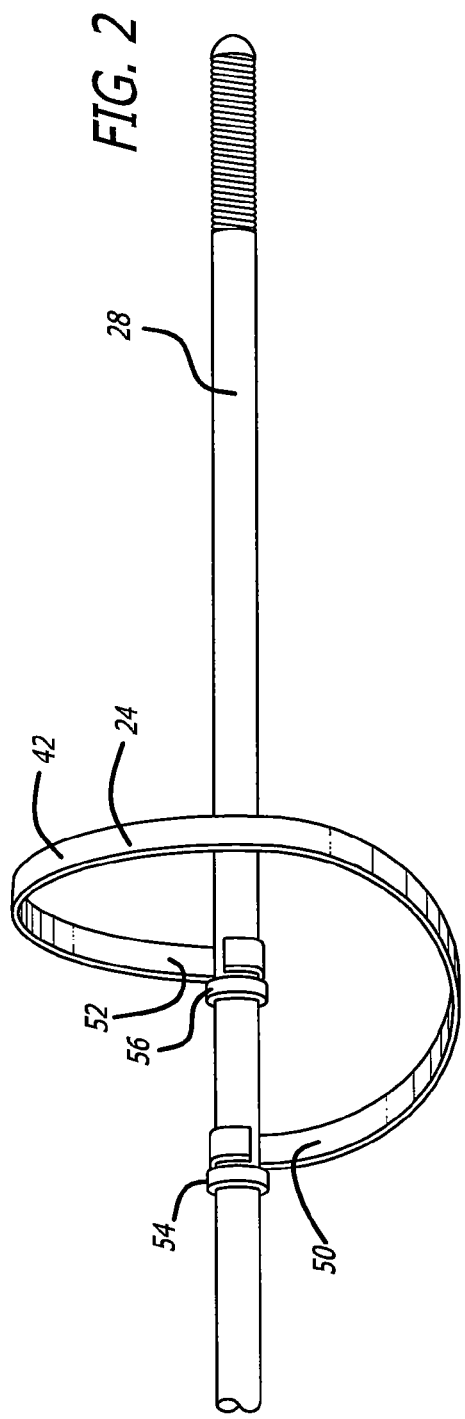

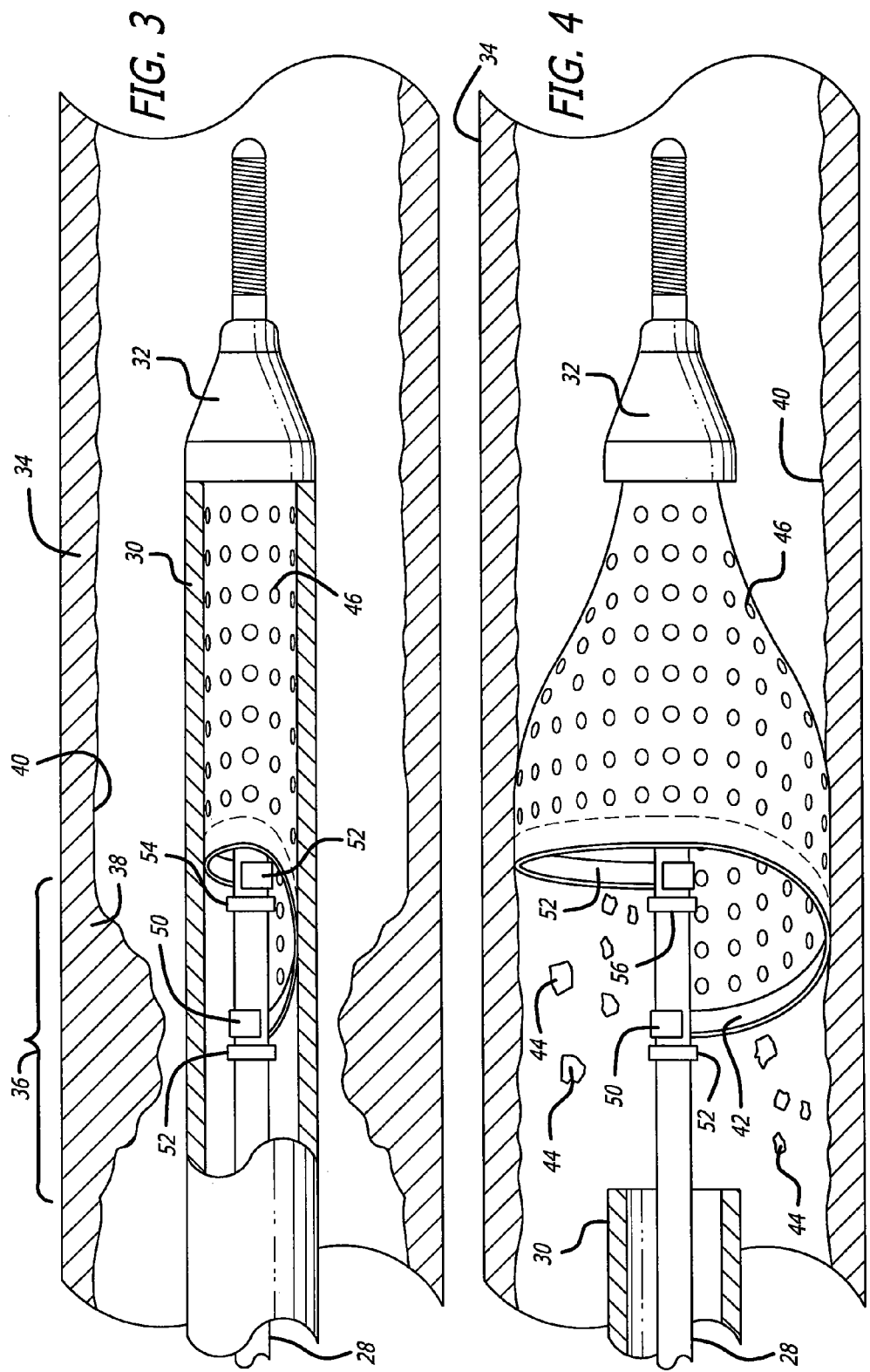

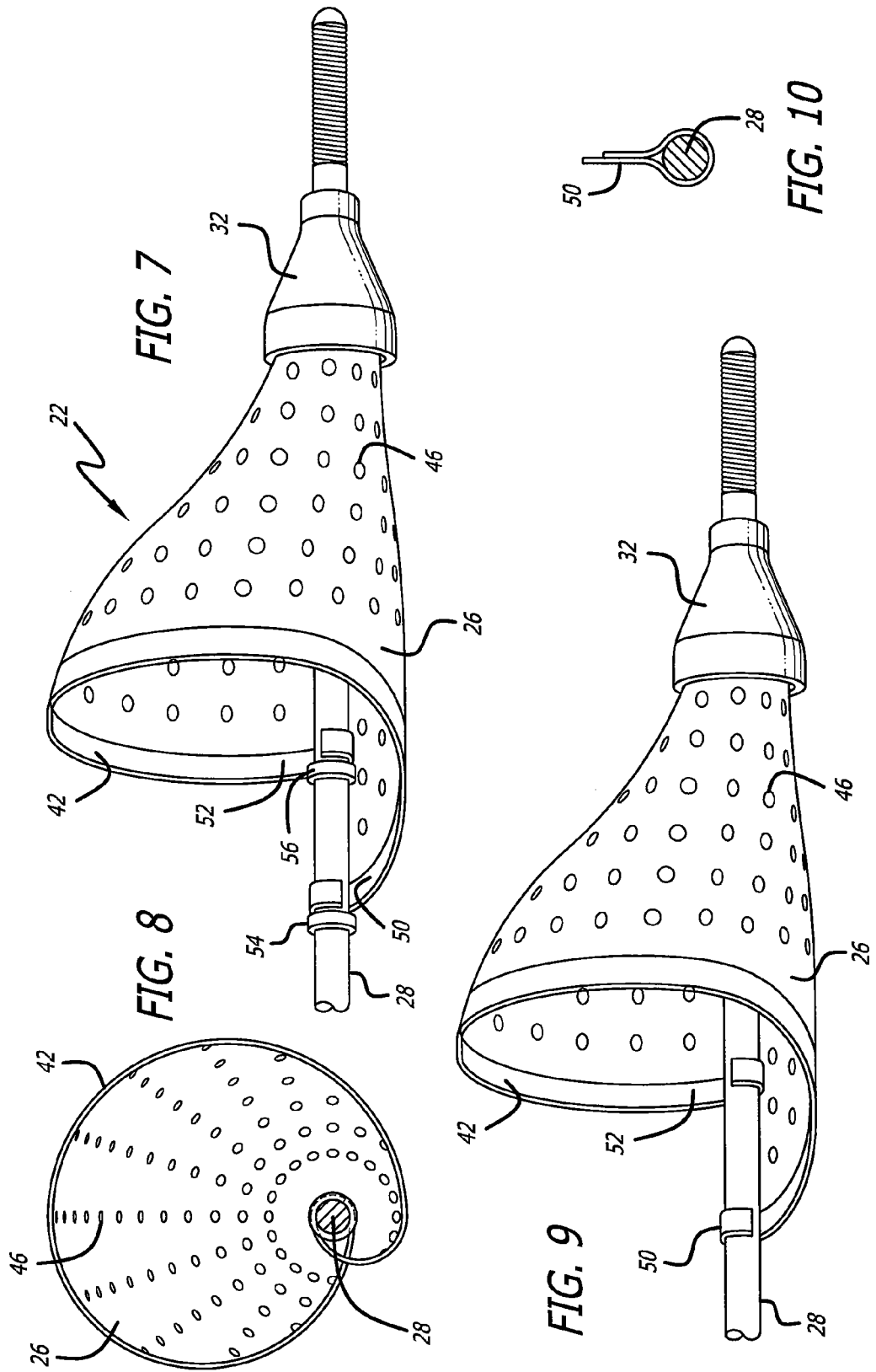

SINGLE-WIRE EXPANDABLE CAGES FOR EMBOLIC FILTERING DEVICES

CROSS-REFERENCE TO RELATED APPLICATIONS

This is a continuation of U.S. Ser. No. 10/285,322, filed Oct. 31, 2002 now abandoned the contents of which are hereby incorporated by reference.

BACKGROUND OF THE INVENTION

The present invention relates generally to filtering devices used when an interventional procedure is being performed in a stenosed or occluded region of a body vessel to capture embolic material that may be created and released into the vessel during the procedure. The present invention is more particularly directed to an embolic filtering device having an expandable cage or basket made from a single wire that possesses good flexibility and bendability during delivery.

Numerous procedures have been developed for treating occluded blood vessels to allow blood to flow without obstruction. Such procedures usually involve the percutaneous introduction of an interventional device into the lumen of the artery, usually by a catheter. One widely known and medically accepted procedure is balloon angioplasty in which an inflatable balloon is introduced within the stenosed region of the blood vessel to dilate the occluded vessel. The balloon dilatation catheter is initially inserted into the patient's arterial system and is advanced and manipulated into the area of stenosis in the artery. The balloon is inflated to compress the plaque and press the vessel wall radially outward to increase the diameter of the blood vessel, resulting in increased blood flow. The balloon is then deflated to a small profile so that the dilatation catheter can be withdrawn from the patient's vasculature and the blood flow resumed through the dilated artery. As should be appreciated by those skilled in the art, while the above-described procedure is typical, it is not the only method used in angioplasty.

Another procedure is laser angioplasty which utilizes a laser to ablate the stenosis by super heating and vaporizing the deposited plaque. Atherectomy is yet another method of treating a stenosed body vessel in which cutting blades are rotated to shave the deposited plaque from the arterial wall. A vacuum catheter is usually used to capture the shaved plaque or thrombus from the blood stream during this procedure.

In the procedures of the kind referenced above, abrupt reclosure may occur or restenosis of the artery may develop over time, which may require another angioplasty procedure, a surgical bypass operation, or some other method of repairing or strengthening the area. To reduce the likelihood of the occurrence of abrupt reclosure and to strengthen the area, a physician can implant an intravascular prosthesis for maintaining vascular patency, commonly known as a stent, inside the artery across the lesion. The stent can be crimped tightly onto the balloon portion of the catheter and transported in its delivery diameter through the patient's vasculature. At the deployment site, the stent is expanded to a larger diameter, often by inflating the balloon portion of the catheter.

The above non-surgical interventional procedures, when successful, avoid the necessity of major surgical operations. However, there is one common problem which can become associated with all of these non-surgical procedures, namely, the potential release of embolic debris into the bloodstream that can occlude distal vasculature and cause significant health problems to the patient. For example, during deployment of a stent, it is possible that the metal struts of the stent can cut into the stenosis and shear off pieces of plaque that can travel downstream and lodge somewhere in the patient's vascular system. Pieces of plaque material are sometimes generated during a balloon angioplasty procedure and become released into the bloodstream. Additionally, while complete vaporization of plaque is the intended goal during laser angioplasty, sometimes particles are not fully vaporized and enter the bloodstream. Likewise, not all of the emboli created during an atherectomy procedure may be drawn into the vacuum catheter and, as a result, enter the bloodstream as well.

When any of the above-described procedures are performed in the carotid arteries, the release of emboli into the circulatory system can be extremely dangerous and sometimes fatal to the patient. Debris carried by the bloodstream to distal vessels of the brain can cause cerebral vessels to occlude, resulting in a stroke, and in some cases, death. Therefore, although cerebral percutaneous transluminal angioplasty has been performed in the past, the number of procedures performed has been somewhat limited due to the justifiable fear of an embolic stroke occurring should embolic debris enter the bloodstream and block vital downstream blood passages.

Medical devices have been developed to attempt to deal with the problem created when debris or fragments enter the circulatory system following vessel treatment utilizing any one of the above-identified procedures. One approach which has been attempted is the cutting of any debris into minute sizes which pose little chance of becoming occluded in major vessels within the patient's vasculature. However, it is often difficult to control the size of the fragments which are formed, and the potential risk of vessel occlusion still exists, making such a procedure in the carotid arteries a high-risk proposition.

Other techniques include the use of catheters with a vacuum source which provides temporary suction to remove embolic debris from the bloodstream. However, as mentioned above, there can be complications associated with such systems if the catheter does not remove all of the embolic material from the bloodstream. Also, a powerful suction could cause trauma to the patient's vasculature.

Another technique which has had some success utilizes a filter or trap downstream from the treatment site to capture embolic debris before it reaches the smaller blood vessels downstream. The placement of a filter in the patient's vasculature during treatment of the vascular lesion can reduce the presence of the embolic debris in the bloodstream. Such embolic filters are usually delivered in a collapsed position through the patient's vasculature and then expanded to trap the embolic debris. Some of these embolic filters are self expanding and utilize a restraining sheath which maintains the expandable filter in a collapsed position until it is ready to be expanded within the patient's vasculature. The physician can retract the proximal end of the restraining sheath to expose the expandable filter, causing the filter to expand at the desired location. Once the procedure is completed, the filter can be collapsed, and the filter (with the trapped embolic debris) can then be removed from the vessel. While a filter can be effective in capturing embolic material, the filter still needs to be collapsed and removed from the vessel. During this step, there is a possibility that trapped embolic debris can backflow through the inlet opening of the filter and enter the bloodstream as the filtering system is being collapsed and removed from the patient. Therefore, it is important that any captured embolic debris remain trapped within this filter so that particles are not released back into the body vessel.

Some prior art expandable filters vessel are attached to the distal end of a guide wire or guide wire-like member which allows the filtering device to be steered in the patient's vasculature as the guide wire is positioned by the physician. Once the guide wire is in proper position in the vasculature, the embolic filter can be deployed to capture embolic debris. The guide wire can then be used by the physician to deliver interventional devices, such as a balloon angioplasty dilatation catheter or a stent delivery catheter, to perform the interventional procedure in the area of treatment. After the procedure is completed, a recovery sheath can be delivered over the guide wire using over-the-wire techniques to collapse the expanded filter for removal from the patient's vasculature.

When a combination of an expandable filter and guide wire is utilized, it is important that the expandable filter portion remains flexible in order to negotiate the often tortuous anatomy through which it is being delivered. An expandable filter which is too stiff could prevent the device from reaching the desired deployment position within the patient's vasculature. As a result, there is a need to increase the flexibility of the expandable filter without compromising its structural integrity once in position within the patient's body vessel. Also, while it is beneficial if the area of treatment is located in a substantially straight portion of the patient's vasculature, sometimes the area of treatment is at a curved portion of the body vessel which can be problematic to the physician when implanting the expandable filter. If the expandable filter portion is too stiff, it is possible that the filter may not fully deploy within the curved portion of the body vessel. As a result, gaps between the filter and vessel wall can be formed which may permit some embolic debris to pass therethrough. Therefore, the filtering device should be sufficiently flexible to be deployed in, and to conform to, a tortuous section of the patient's vasculature, when needed.

Another problem presented to a physician utilizing an embolic filtering device is the possible undesired collection of embolic debris on the struts or ribs that form the cage onto which the filter is attached. The exposed surface of proximally located struts provide a potential area where embolic debris can stick, never reaching the filter positioned downstream from these struts. As the embolic filtering device is being collapsed for removal from the patient, it is possible for embolic debris which has become stuck to these struts to become dislodged and enter the blood stream. As a result, the design of the embolic filtering device itself may pose a danger if too many struts are located proximal to the filter since increased surface area will be exposed to the embolic particles. Therefore, it may be beneficial to use thin struts in the proximal region of the filtering device or to reduce the number of struts forming the self-expanding cage.

What has been needed is an expandable filter assembly having high flexibility and bendability with sufficient strength to be successfully deployed within a patient's vasculature to collect embolic debris which may be released into the patient's vasculature. Moreover, it would be beneficial if the design of the filtering device reduces the chances of embolic debris becoming stuck to the struts of the device, rather than being trapped within the filter. The present invention disclosed herein satisfies these and other needs.

SUMMARY OF THE INVENTION

The present invention provides a flexible, single-wire cage for use with an embolic filtering device designed for capturing, for example, embolic debris created during the performance of a therapeutic interventional procedure, such as a balloon angioplasty or stenting procedure, within a body vessel. The present invention provides the physician with an embolic filtering device having good flexibility to be steered through tortuous anatomy while possessing sufficient strength to hold open a filtering element against the wall of the body vessel for capturing embolic debris. An embolic filtering device made in accordance with the present invention is relatively easy to deploy and is easily conformable to the patient's anatomy.

An embolic filtering device made in accordance with the present invention utilizes a single wire to create an expandable cage. The single-wire cage can be made from a self-expanding material, for example, nickel-titanium (NiTi), and is capable of expanding from a collapsed position or configuration having a first delivery diameter to an expanded or deployed position or configuration having a second implanted diameter. A filter element made from an embolic-capturing material is attached to the single-wire cage to move between the unexpanded position and a deployed position.

In one aspect of the present invention, the cage wire is coupled to the distal end of an elongated member, such as a guide wire, and is adapted to expand and conform to the size and shape of the body vessel in which it is deployed. The cage wire has one end which is coupled to the guide wire and a second end that is likewise coupled to the guide wire. In one particular aspect of the invention, the first and second ends of the cage can be rotatably mounted to the guide wire. The first end and second end of the cage wire are positioned longitudinally away from each other a certain distance to allow a spiral configuration to be formed as the wire unfurls into the expanded position. The spiral created by the cage wire is adapted to conform within the body vessel of the patient. A filter element is, in turn, attached to the single-wire cage and will contact the wall of the body vessel wall once deployed within the patient. The cage wire can be extremely thin wire, or alternately, a wire ribbon having an expanded width that provides additional surface area onto which the filter member can be attached. The filter member can be attached to the single-wire cage, for example, by bonding or other attachment techniques well-known in the art.

In another aspect of the present invention, the single-wire cage is not only rotatably mounted onto the guide wire, but has one end fixed between a pair of stop fittings that limit the longitudinal travel of the single-wire cage on the guide wire itself. In this regard, the single-wire cage will be both rotatably mounted onto the guide wire and will have a limited range of longitudinal motion along the guide wire as well. In this regard, if the proximal end of the guide wire is moved or rotated by the physician, the deployed single-wire cage and filter should remain stationary within the body vessel and should not move with the guide wire.

In another aspect of the present invention, the single-wire cage is mounted onto the guide wire such that the guide wire remains substantially centered within the body vessel once the cage is deployed. In yet another aspect of the present invention, the single-wire cage remains offset from the center of the body vessel when deployed. The cage is said to be "offset" in that the guide wire extends substantially along the vessel wall of the patient, rather than being "centered" in the body vessel when the single-wire cage is expanded. In this offset position, there is little cage structure directly in front of the filter member once deployed in the open vessel, resulting in a virtually unobstructed opening for the filter element. The first and second ends of the single-wire cage can be rotatably connected to the guide wire in this offset cage arrangement such that the cage wire spirals when expanded to provide and maintain a satisfactory opening for the filter member. In this arrangement, the single-wire cage will still conform to the particular size and shape of the body vessel once implanted.

The single-wire cage can be "set" to remain in the expanded, deployed position until an external force is placed over the cage wire to collapse and move the cage wire to a collapsed position. One way of accomplishing this is through the use of a restraining sheath, for example, which can be placed over the filtering device in a coaxial fashion to contact the single-wire cage and move the cage into the collapsed position. The guide wire and filtering assembly, with the restraining sheath placed over the filter assembly, can be delivered through the patient's vasculature to the target location. Once the physician properly manipulates the guide wire into the target area, the restraining sheath can be retracted to deploy the single-wire cage into the expanded position. This can be easily performed by the physician by simply retracting the proximal end of the restraining sheath. Once the restraining sheath is retracted, the self-expanding properties of the single-wire cage cause the cage wire to move in an outward, radial fashion away from the guide wire to contact the wall of the body vessel. As the cage wire expands radially, so does the filter element which will now be maintained pressed against the vessel wall to collect embolic debris that may be released into the bloodstream as the physician performs the interventional procedure. The guide wire can be used by the physician to deliver the necessary interventional device into the area of treatment. The deployed filter element captures embolic debris created and released into the body vessel during the interventional procedure. A retrieval sheath can be delivered over the guide wire to collapse the filter assembly for removal from the patient.

In another aspect of the present invention, the single-wire cage has a "windsock" type of filter design that possesses good flexibility and bendability, yet possesses sufficient radial strength to maintain the filtering element in an open position once deployed in the body vessel.

In another aspect of the present invention, the filtering assembly, which includes the single-wire cage and filter element, is moveable in a coaxial fashion over the guide wire so as to permit the guide wire to be first steered into the target area by the physician, with the filtering assembly being delivered later to the desired location along the guide wire in an over-the-wire fashion. In this regard, the filtering assembly is maintained in a collapsed delivery position by a restraining sheath or other restraining device so that it may be delivered over the guide wire to the exact location where the filtering capabilities of the device is needed. This over-the-wire feature can be implemented with the embodiment of the single-wire cage in which the guide wire is centered within the body lumen once the cage is deployed or the offset version in which the guide wire remains at an offset location near the side wall of the body lumen.

It is to be understood that the present invention is not limited by the embodiments described herein. The present invention can be used in arteries, veins, and other body vessels. Other features and advantages of the present invention will become more apparent from the following detailed description of the invention, when taken in conjunction with the accompanying exemplary drawings.

BRIEF DESCRIPTION OF THE DRAWINGS

FIG. 1 is a side elevational view of an embolic filtering device having a single-wire cage embodying features of the present invention.

FIG. 2 is a side elevational view of the single-wire cage of FIG. 1 in its expanded configuration with the filter element removed to better show the single-wire cage.

FIG. 3 is an elevational view, partially in cross section, of the embolic filtering device of FIG. 1 as it is being delivered within a body vessel to a location downstream from an area to be treated.

FIG. 4 is an elevational view, partially in cross section, similar to that shown in FIG. 3, wherein the embolic filtering device is deployed in its expanded position within the body vessel for filtering purposes.

FIG. 7 is a side elevational view of an embodiment of an embolic filtering device having an offset, single-wire cage which embodies features of the present invention.

FIG. 8 is an end view of the single-wire cage of FIG. 7 in its fully expanded position.

FIG. 9 is a side elevational view of yet another embodiment of an embolic filtering device having an offset, single-wire cage which embodies features of the present invention.

FIG. 10 is cross-sectional view of the guide wire and one end of the single-wire cage as it is securely fastened to the guide wire.

DETAILED DESCRIPTION OF THE PREFERRED EMBODIMENTS

Figure 5B:
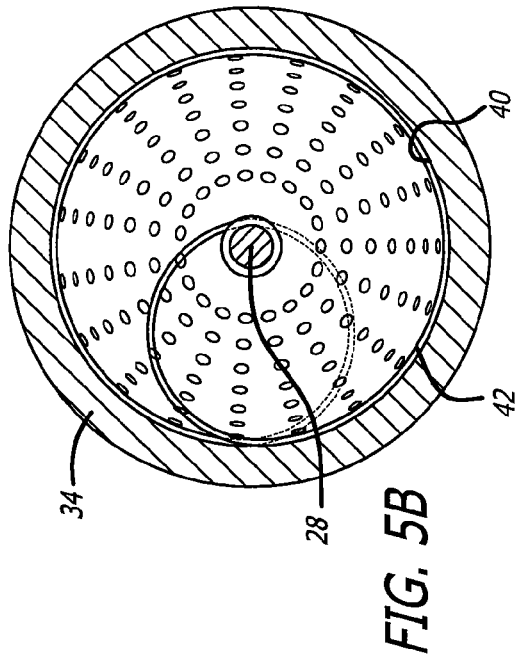
FIG. 5B is a cross-sectional end view of the single-wire cage of FIG. 1 in its deployed, expanded position within a body vessel.

Turning now to the drawings, in which like reference numerals represent like or corresponding elements in the drawings, FIGS. 1 and 2 illustrate one particular embodiment of an embolic filtering device 20 incorporating features of the present invention. This embolic filtering device 20 is designed to capture embolic debris which may be created and released into a body vessel during an interventional procedure. The embolic filtering device 20 includes an expandable filter assembly 22 having a self-expanding, single-wire cage 24 and a filter element 26 attached thereto. In this particular embodiment, the expandable filter assembly 22 is rotatably mounted on the distal end of an elongated (solid or hollow) cylindrical tubular shaft, such as a guide wire 28. The expandable filter assembly also could be attached directly onto the guide wire, so as not to rotate independently of the guide wire. The guide wire has a proximal end (not shown) which extends outside the patient and is manipulated by the physician to deliver the filter assembly into the target area in the patient's vasculature. A restraining or delivery sheath 30 (FIG. 3) extends coaxially along the guide wire 28 in order to maintain the expandable filter assembly 22 in its collapsed position until it is ready to be deployed within the patient's vasculature. The expandable filter assembly 22 can be deployed by the physician by simply retracting the restraining sheath 30 proximally to expose the expandable filter assembly. Once the restraining sheath is retracted, the single-wire cage 24 immediately begins to expand within the body vessel (see FIG. 4), causing the filter element 26 to expand as well.

An obturator 32 affixed to the distal end of the filter assembly 32 can be implemented to prevent possible "snowplowing" of the embolic filtering device as it is being delivered through the vasculature. The obturator can be made from a soft polymeric material, such as Pebax 40D, and has a smooth surface to help the embolic filtering device travel through the vasculature and cross lesions while preventing the distal end of the restraining sheath 30 from "digging" or "snowplowing" into the wall of the body vessel.

In FIGS. 3 and 4, the embolic filtering device 20 is shown as it is being delivered within an artery 34 or other body vessel of the patient. Since the embolic filtering device made in accordance with the present invention possesses excellent bendability and flexibility, it will conform well to the shape of the vasculature while allowing the filter assembly to more easily negotiate a curved radius in the patient's vasculature.

Referring specifically now to FIG. 4, the embolic filtering device 20 is shown in its expanded position within the patient's artery 34. This portion of the artery (FIG. 3) has an area of treatment 36 in which atherosclerotic plaque 38 has built up against the inside wall 40 of the artery 34. The filter assembly 22 is to be placed distal to, and downstream from, the area of treatment 36. For example, the therapeutic interventional procedure may comprise the implantation of a stent (not shown) to increase the diameter of an occluded artery and increase the flow of blood therethrough. It should be appreciated that the embodiments of the embolic filtering device described herein are illustrated and described by way of example only and not by way of limitation. Also, while the present invention is described in detail as applied to an artery of the patient, those skilled in the art will appreciate that it can also be used in other body vessels, such as the coronary arteries, carotid arteries, renal arteries, saphenous vein grafts and other peripheral arteries. Additionally, the present invention can be utilized when a physician performs any one of a number of interventional procedures, such as balloon angioplasty, laser angioplasty or atherectomy which generally require an embolic filtering device to capture embolic debris created during the procedure.

The cage 24 includes a single cage wire 42 which, upon release from the restraining sheath 30, expands the filter element 26 into its deployed position within the artery (FIG. 4). Embolic particles 44 created during the interventional procedure and released into the bloodstream are captured within the deployed filter element 26. The filter may include perfusion openings 46, or other suitable perfusion means, for allowing blood flow through the filter element 26. The filter element will capture embolic particles which are larger than the perfusion openings while allowing some blood to perfuse downstream to vital organs. Although not shown, a balloon angioplasty catheter could be initially introduced within the patient's vasculature in a conventional SELDINGER technique through a guiding catheter (not shown). The guide wire 28 is disposed through the area of treatment and the dilatation catheter can be advanced over the guide wire 28 within the artery 34 until the balloon portion is directly in the area of treatment 36. The balloon of the dilatation catheter can be expanded, expanding the plaque 38 against the wall 40 of the artery 34 to expand the artery and reduce the blockage in the vessel at the position of the plaque 38. After the dilatation catheter is removed from the patient's vasculature, a stent (not shown) could be implanted in the area of treatment 36 using over-the-wire or rapid exchange techniques to help hold and maintain this portion of the artery 34 and help prevent restenosis from occurring in the area of treatment. The stent could be delivered to the area of treatment on a stent delivery catheter (not shown) which is advanced from the proximal end of the guide wire to the area of treatment. Any embolic debris created during the interventional procedure will be released into the bloodstream and should enter the filter 26. Once the procedure is completed, the interventional device may be removed from the guide wire. The filter assembly 22 can also be collapsed and removed from the artery 34, taking with it any embolic debris trapped within the filter element 26. A recovery sheath (not shown) can be delivered over the guide wire 28 to collapse the filter assembly 22 for removal from the patient's vasculature.

Referring again to FIGS. 1 and 2, the single-wire cage 24 is made from a single-cage wire 42 which has a first end 50 and a second end 52 attached to the guide wire 28. The cage wire 42 is shown as a ribbon wire which has additional width that provides an additional bonding area for attaching the filter element 26 thereto. It should be appreciated that the size of the width of this cage wire 42 can vary from a very thin width to a width which is even greater than that shown in FIGS. 1 and 2. The size and width of the cage wire 42 can accordingly vary as is needed for a particular application. Additionally, the size and width, and even thickness of the cage wire 42, can be varied depending upon the particular material which is utilized in manufacturing of the wire.

The single-wire cage 24 of the present invention is shown rotatably mounted to the distal end of the guide wire 28 to allow the entire filter assembly 22 to remain stationary once deployed in the body vessel. In this regard, the first end 50 and second end 52 are shown rotatably mounted to the guide wire 28. This feature prevents the filtering assembly from rotating against the wall of the body vessel in the event that the proximal end of the guide wire should be rotated by the physician during use. As a result, the possibility that movement of the proximal end of the guide wire could translate to the deployed filter assembly 22 is prevented. Therefore, trauma to the wall of the body vessel is minimized. Referring again to FIGS. 1 and 2, a pair of stop fittings 54 and 56 are placed on the guide wire to maintain the first end 50, and hence the proximal end of the single-wire cage 24, rotatably fixed to the guide wire 28. These stop fittings 54 and 56 allow the cage 24 to spin on the guide wire while restricting the longitudinal movement of the cage on the guide wire. As can be seen in FIG. 1, the first end 50 of the cage wire 42 can move between the stop fittings 54 and 56 to allow the cage to have at least some longitudinal movement on the guide wire. Alternatively, stop fitting 56 can be moved proximally on the guide wire to prevent longitudinal motion of the first end 50, while still permitting rotation. It should be appreciated that the second end 52 of the cage wire 42 is also movable in the longitudinal direction of the guide wire in order to move between the expanded and unexpanded positions. Stop fittings could also be used to limit, or prevent, longitudinal travel of the second end 52 along the guide wire as well. Accordingly, it may be preferred to have the obturator 32 slidably disposed along the guide wire as well to allow it to rotate and move longitidinally along the guide wire when moving between the unexpanded and expanded positions. This particular mechanism is just one way in which the single-wire cage 24 can be mounted to the guide wire 28. Other embodiments disclosed herein can use similar stop fittings as those described above. Alternatively, the expandable cage can be attached directly onto the guide wire so as not to rotate independently.

Figure 5A:
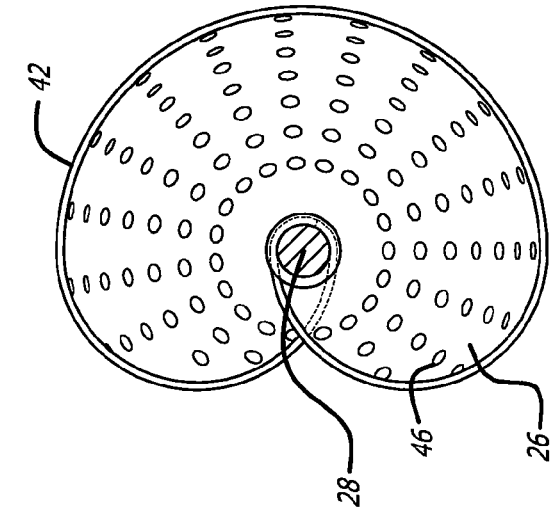
FIG. 5A is an end view of the single-wire cage of FIG. 1 in its fully expanded position.

Referring now to FIGS. 5A and 5B, an end view of the opening of the filter element 26 is shown. Referring particularly to FIG. 5A, the end view shows the single-wire cage 24 as it extends in its most radially expanded position outside of a body lumen. As can be seen in FIG. 5A, the opening created by the single-wire cage 24 is not perfectly round, but has a somewhat elliptical shape. However, once implanted within the body lumen, as is schematically shown in FIG. 5B, the single-wire cage adapts to the size of the body lumen such that the single-wire cage becomes more circular to ensure that there are no gaps formed between the filter element and the wall of the body lumen. In this regard, the first and second ends of the cage wire 42 rotate on the guide wire which allows the single-wire cage to assume a more circular shape once implanted in the body lumen. As a result, there is little chance of gaps being formed between the filter element and the wall of the body vessel.

Figure 6:
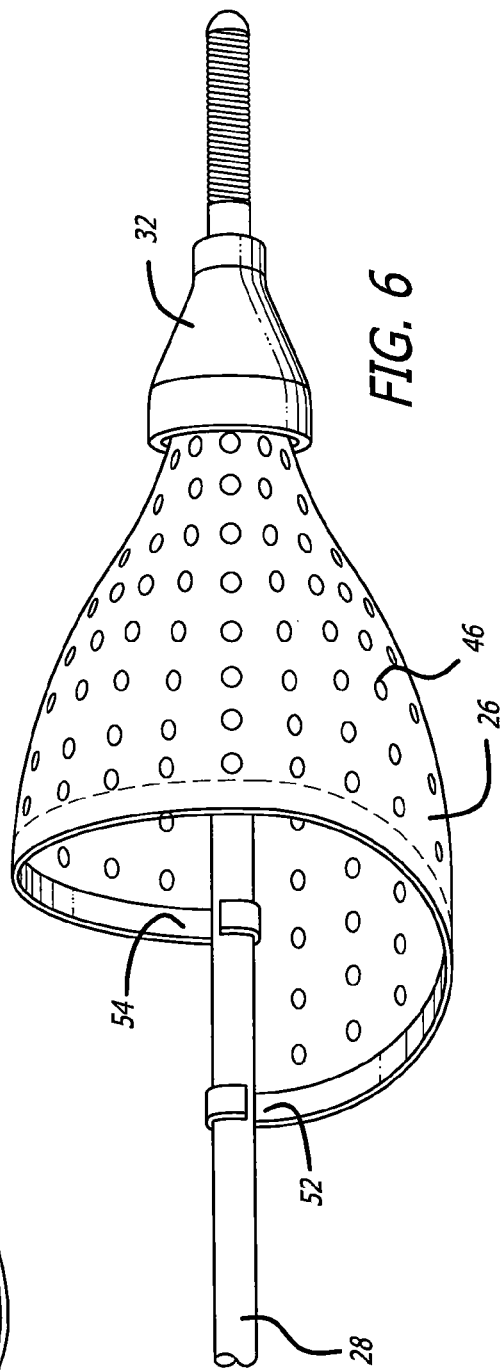
FIG. 6 is a side elevational view of another embodiment of an embolic filtering device having a single-wire cage which embodies features of the present invention.

Referring now to FIG. 6, an alternative embodiment of the filtering device 20 is shown. In this particular embodiment, the single-wire cage 24 is shown again rotatably mounted to the guide wire 28, however, this particular embodiment lacks the pair of stop fittings which were used on the previously described embodiment shown in FIGS. 1-4. This will allow the entire filter assembly 22 to move along the length of the guide wire and in fact can be delivered over the guide wire as a separate filtering element after the guide wire is initially positioned within the patient's vasculature. In such an arrangement, the guide wire is first steered into the target area and then the filter assembly can be delivered over the guide wire as it is maintained in its unexpanded, delivery position by a delivery sheath or other restraining device. The distal end of the filter assembly would have to come in contact with a stop fittings or fastener (not shown) which could be located at the distal end of the guide wire which contacts the filter assembly to prevent it from being delivered past the distal end of the guide wire. In such an arrangement, an over-the-wire filtering system can be utilized. It should also be appreciated that the first and second ends of the single-wire cage could also be permanently attached to the guide wire 26 to create a permanent filter/guide wire assembly.

Referring now to FIGS. 7-9, several alternative embodiments of the filtering device 20 are shown. Referring initially to FIG. 7, the filtering device 20 is shown as an offset assembly in which the guide wire 28 will remain close to the wall of the body vessel once implanted within the patient. This particular embodiment differs from the one shown in FIGS. 1-6 in that the guide wire 28 would not be centered in the body vessel when implanted. Rather, it would again remain closer to the side wall of the body vessel. This particular embodiment has some advantages in that the opening of the filter element 26 is unimpeded by any portion of the expandable cage since the expandable cage also remains extended along the periphery of the vessel wall once implanted. Reference should be given to FIG. 8 which shows the expanded single-wire cage in its fully expanded position. As can be seen in FIG. 8, there is virtually no portion of the single-wire cage that would block the opening of the filter element. FIG. 8 is similar to FIG. 5A in that the single-wire cage 24 is shown in its fully expanded position. It should be appreciated that once implanted into a smaller diameter body vessel, the single-wire cage will conform to the wall of the vessel in a manner which is similar to that shown in FIG. 5B.

FIG. 9 shows another embodiment of the offset filter assembly of FIG. 7 except that the stop fittings have been removed from the guide wire to allow the filter assembly to be slidably disposed on the guide wire. This particular embodiment of the filtering assembly is again similar to that shown in FIG. 6 in that the filter assembly could either be permanently attached to the guide wire or could be slid and delivered across the guide wire in a coaxial fashion after the guide wire has been steered into the desired area of the patient's vasculature. This particular embodiment, as shown in FIG. 9, provides the benefits of an offset cage with the ability to slide the entire filter assembly over the guide wire in an over-the-wire fashion.

Referring now to FIG. 10, the first end 50 of the cage wire 42 is shown as it is attached to the guide wire 28. In this particular figure, the first end 50 is shown as it extends around the guide wire 28 and is looped and attached back onto itself, via a bonding, soldering, braising, or other fastening technique, to help prevent the end of the cage wire from being accidentally removed from the guide wire. The previous embodiments of the filtering assembly show the first and second ends of the cage wire attached to the guide wire in a loop fashion which helps to maintain the single-wire cage on the guide wire. The particular arrangement of the end of the cage wire, as shown in FIG. 10, helps to prevent the wire from being accidentally removed from the wire during use. Such a particular arrangement is particularly useful in the event that the filter assembly is being slid over the guide wire in a coaxial fashion when used in accordance with the embodiments shown in FIGS. 6 and 9. Again, this is just one way in which the ends of the cage wire can be physically attached to the guide wire.

The expandable cage of the present invention can be made in many ways. One particular method of making the cage is to cut a thin-walled tubular member, such as nickel-titanium hypotube, to remove portions of the tubing in the desired pattern, leaving relatively untouched the portions of the tubing which form the single-wire structure. The tubing may be cut into the desired pattern by means of a machine-controlled laser. The tubing used to make the cage could possible be made of suitable biocompatible material, such as spring steel. Elgiloy is another material which could possibly be used to manufacture the cage. Also, very elastic polymers possibly could be used to manufacture the single-wire cage.

The thickness of the wire is often very small, so the tubing from which the single-wire cage is made may have a small diameter. Typically, the tubing has an outer diameter on the order of about 0.020-0.040 inches in the unexpanded condition. Also, the cage can be cut from large diameter tubing. Fittings are attached to both ends of the lased tube to form the final cage geometry. The wall thickness of the tubing is usually about 0.076 mm (0.001-0.010 inches). As can be appreciated, the strut width and/or depth at the bending points will be less. For cages deployed in body lumens, such as PTA applications, the dimensions of the tubing may be correspondingly larger. While it is preferred that the cage be made from laser cut tubing, those skilled in the art will realize that the cage can be laser cut from a flat sheet and then rolled up in a cylindrical configuration to form the spiral shape of the cage wire. The single-wire cage can also be used by just setting a piece of wire, or wire ribbon, with the desired spiral shape that the wire makes when attached to the guide wire. In this regard, the final expanded diameter could be set into the material.

The single-wire cage can be laser cut much like a stent is laser cut. Details on how the tubing can be cut by a laser are found in U.S. Pat. Nos. 5,759,192 (Saunders), 5,780,807 (Saunders) and 6,131,266 (Saunders) which have been assigned to Advanced Cardiovascular Systems, Inc.

Nickel-titanium alloy is yet another material which can be used to from the single-wire cage due to the self-expanding properties such a material possesses. A suitable composition of nickel-titanium which can be used to manufacture the single-wire cage of the present invention is approximately 55% nickel and 45% titanium (by weight) with trace amounts of other elements making up about 0.5% of the composition. The austenite transformation temperature is between about 0° C. and 20° C. in order to achieve superelasticity at human body temperature. The austenite temperature is measured by the bend and free recovery tangent method. The upper plateau strength is about a minimum of 60,000 psi with an ultimate tensile strength of a minimum of about 155,000 psi. The permanent set (after applying 8% strain and unloading), is less than approximately 0.5%. The breaking elongation is a minimum of 10%. It should be appreciated that other compositions of nickel-titanium can be utilized, as can other self-expanding alloys, to obtain the same features of a self-expanding cage made in accordance with the present invention.

In one example, the cage of the present invention can be laser cut from a tube of nickel-titanium (Nitinol) whose transformation temperature is below body temperature. After the wire pattern is cut into the hypotube, the tubing is expanded and heat treated to be stable at the desired final diameter. The heat treatment also controls the transformation temperature of the cage such that it is super elastic at body temperature. The transformation temperature is at or below body temperature so that the cage is superelastic at body temperature. The cage is usually implanted into the target vessel which is smaller than the diameter of the cage in its fully expanded position so that the single-wire cage can apply a force to the vessel wall to maintain the cage and filter element in its expanded position. It should be appreciated that the single-wire cage can be made from either superelastic, stress-induced martensite NiTi or shape-memory NiTi.

The cage also could be manufactured by laser cutting a large diameter tubing of nickel-titanium which would create the cage in its expanded position. Thereafter, the formed cage could be placed in its unexpanded position by backloading the cage into a restraining sheath which will keep the device in the unexpanded position until it is ready for use. If the cage is formed in this manner, there would be no need to heat treat the tubing to achieve the final desired diameter. This process of forming the cage could be implemented when using superelastic or linear-elastic nickel-titanium.

The polymeric material which can be utilized to create the filtering element include, but is not limited to, polyurethane and Gortex, a commercially available material. Other possible suitable materials include ePTFE. The material can be elastic or non-elastic. The wall thickness of the filtering element can be about 0.00050-0.0050 inches. The wall thickness may vary depending on the particular material selected. The material can be made into a cone or similarly sized shape utilizing blow-mold technology or dip molding technology. The openings can be any different shape or size. A laser, a heated rod or other process can be utilized to create to perfusion openings in the filter material. The holes, would of course be properly sized to catch the particular size of embolic debris of interest. Holes can be lazed in a spinal pattern with some similar pattern which will aid in the re-wrapping of the media during closure of the device. Additionally, the filter material can have a "set" put in it much like the "set" used in dilatation balloons to make the filter element re-wrap more easily when placed in the collapsed position.

The materials which can be utilized for the restraining sheath can be made from polymeric material such as cross-linked HDPE. This sheath can alternatively be made from a material such as polyolifin which has sufficient strength to hold the compressed strut assembly and has relatively low frictional characteristics to minimize any friction between the filtering assembly and the sheath. Friction can be further reduced by applying a coat of silicone lubricant, such as Microglide®, to the inside surface of the restraining sheath before the sheaths are placed over the filtering assembly.

Further modifications and improvements may additionally be made to the device and method disclosed herein without departing from the scope of the present invention. Accordingly, it is not intended that the invention be limited, except as by the appended claims.

What is claimed is:

1. An embolic filtering device for capturing embolic debris in a body fluid flowing within a body vessel, comprising:
   a guide wire having a proximal stop fitting and an intermediate stop fitting fixedly attached thereto;
   a support frame having a pre-deployment collapsed position and a deployed expanded position, wherein the support frame is made from a length of a single, continuous wire having a first end slidably attached to the guide wire between the proximal stop fitting and the intermediate stop fitting and a second end slidably attached to the guide wire at a location distal to the intermediate stop fitting; and
   a filtering element having a proximal inlet opening and a plurality of distal outlet openings, the outlet openings allowing the body fluid to flow through the filtering element but retaining embolic debris within the filtering element, and the inlet opening being larger than the outlet openings, wherein the entire length of the support frame is attached to opening the proximal opening of the filtering element to open the filtering element when the support frame is in the deployed expanded position.

2. The embolic filtering device of claim 1, wherein the support frame forms a spiral shape when placed in the expanded position.

3. The embolic filtering device of claim 1, wherein the first and second ends of the support frame are movable along the longitudinal axis of the guide wire.

4. The embolic filtering device of claim 1, wherein the support frame is made from a self-expanding material.

5. The embolic filtering device of claim 1, wherein the first end and second end of the support frame are rotatably mounted to the guide wire.

6. The embolic filtering device of claim 1, wherein the support frame forms a substantially spiral loop when placed in the deployed expanded position and the guide wire extends substantially in the center of the formed spiral loop.

7. The embolic filtering device of claim 1, wherein the support frame forms a substantially spiral loop when placed in the deployed expanded position and the guide wire extends substantially along the periphery of the formed spiral loop.

8. The embolic filtering device of claim 1, wherein the wire forming the support frame is a wire ribbon.

9. The embolic filtering device of claim 1, wherein the wire ribbon is made from a nickel-titanium alloy.

10. The embolic filtering device of claim 8, wherein the support frame forms a spiral when placed in the deployed expanded position.

11. The embolic filtering device of claim 1, wherein the first and second ends of the support frame form hoops which extend around the guide wire.

12. The filtering device of claim 1, wherein the support frame is movable between its expanded and unexpanded positions through relative longitudinal movement between the first end and second end of the wire.

13. An embolic filtering device for capturing embolic debris in a body fluid flowing within a body vessel, comprising:
   a guide wire having a proximal stop fitting and an intermediate stop fitting fixedly attached thereto;
   a support frame having a pre-deployment collapsed position and a deployed expanded position, the support frame having a first end slidably attached to the guide wire between the proximal stop fitting and the intermediate stop fitting and a second end slidably attached to the guide wire at a location distal to the intermediate stop fitting; and a filtering element having a proximal edge forming an inlet opening and a plurality of distal outlet openings, the outlet openings allowing the body fluid to flow through the filtering element but retaining embolic debris within the filtering element, and the inlet opening being larger than the outlet openings, wherein the entire support frame is attached to the proximal edge of the filtering element.

14. The embolic filtering device of claim 13, wherein the first and second ends of the support frame are movable along the longitudinal axis of the guide wire.

15. The embolic filtering device of claim 13, wherein the support frame is made from a self-expanding material.

16. The embolic filtering device of claim 13, wherein the first end and second end of the support frame are rotatably mounted to the guide wire.

17. The embolic filtering device of claim 13, wherein the support frame forms a spiral when placed in the deployed expanded position.

18. The embolic filtering device of claim 13, wherein the intermediate stop is located between the first end and the second end of the support frame.

19. The filtering device of claim 13, wherein the support frame is movable between its expanded and unexpanded positions through relative longitudinal movement between the first end and second end of the support frame.

20. The embolic filtering device of claim 13, wherein filtering element is attached to the support frame.

* * * * *